United States Patent [19]

Goeddel

[11] 4,456,748
[45] Jun. 26, 1984

[54] HYBRID HUMAN LEUKOCYTE INTERFERONS

[75] Inventor: David V. Goeddel, Burlingame, Calif.

[73] Assignee: Genentech, Inc., South San Francisco, Calif.

[21] Appl. No.: 305,657

[22] Filed: Sep. 25, 1981

Related U.S. Application Data

[63] Continuation-in-part of Ser. No. 237,388, Feb. 23, 1981, Pat. No. 4,414,150, and Ser. No. 205,579, Nov. 10, 1980, abandoned.

[51] Int. Cl.[3] .................. C12N 15/00; C12N 1/20; C12N 1/00; C07H 21/04; C12P 21/00; C12P 21/02; C12P 19/34
[52] U.S. Cl. ................................. 536/27; 435/172.3; 435/253; 435/317; 435/811; 435/68; 435/70; 435/91
[58] Field of Search ............... 435/68, 70, 91, 172, 435/253, 317; 536/27

[56] References Cited

U.S. PATENT DOCUMENTS 4,262,090 4/1981 Colby et al. ............ 435/68

OTHER PUBLICATIONS

Derynck et al., Nature 285, 542, (1980).
Nagata et al., Nature 284, 316, (1980).
Taniguchi et al., Proc. Japan. Acad. 55, Ser. B, 464, (1979).
Nienhuis et al., New Eng. J. Med. 297, 1318, (1977).
Miozzari et al., Nature 277, 486, (1979).
Research Disclosure, Jul. 1979, pp. 351-352, 1351.
Itakura et al., Science 196, 1056, (1977).

Primary Examiner—Thomas G. Wiseman
Assistant Examiner—James Martinell
Attorney, Agent, or Firm—Jon S. Saxe; George M. Gould; Steve T. Zelson

[57] ABSTRACT

Disclosed herein are methods and means of microbially preparing novel human hybrid leukocyte interferons, useful in the treatment of viral and neoplastic diseases, by DNA recombination of parental interferon genes, taking advantage of common restriction endonuclease cleavage sites therein and in carrier expression plasmids.

5 Claims, 9 Drawing Figures

```
               -60              -40              -20              +1               20               40
                 ,                ,                ,                ,                ,                ,
LeIF A  TGAGCCTAAACCTTAGGCTCACCCATTTCAACCAGTCTAGCAGCATCTGCAACATCTACAATGGCCTTGACCTTTGCTTTACTGGTGGCCCTCCTGGTGC
LeIF B                                TACTAGCTCAGCAGCATCCGCAACATCTACAATGCCTTGACTTTTTATTTAATGGTGGCCCTAGTGGTGC
LeIF C             CAAGGTTATCCATCTCAAGTAGCCTAGCAATATTTGCAACATCCCAATGCCCTGTCCTTTTCTTTACTTATGGCCGTGCTGGTGC
LeIF D             CAAGGTTCAGAGTCACCCATCTCAGCAAGCCCAGAAGTATCTGCAATATCTACGATGGCCTCGGCCCTTTGCTTTACTGATGGTCCTGGTGGTGC
LeIF E
LeIF F                                                       ACATCCCAATGGCCCTGTCCTTTTCTTTACTGATGGCCGTGCTGGTGC
LeIF G
LeIF H       CCAAGGTTCAGTGTTACCCCTCATCAACCAGCCCAGCAGCATCTTCGGGATTCCCAATGGCATTGCCCTTTGCTTTAATGATGGCCCTGGTGGTGC 60               80              100              120              140
                  ,                ,                ,                ,                ,
LeIF A  TCAGCTGCAAGTCAAGCTGCTCTGTGGGCTGTGATCTGCCTCAAACCCACAGCCTGGGTAGCAGGAGGACCTTGATGCTCCTGGCACAGATGAGGAAAAT
LeIF B  TCAGCTACAAGTCATTCAGCTCTCTGGGCTGTGATCTGCCTCAGACTCACAGCCTGGGTAACAGGAGGGCCTTGATACTCCTGGCACAAATGCGAAGAAT
LeIF C  TCAGCTACAAATCCATCTGTTCTCTGGGCTGTGATCTGCCTCAGACCCACAGCCTCGGTAATAGGAGGGCCTTGATACTCCTGGGACAAATGGGAAGAAT
LeIF D  TCAGCTGCAAGTCAAGCTGCTCTCTGGGCTGTGATCTCCCTGAGACCCACAGCCTGGATAACAGGAGGACCTTGATGCTCCTGGCACAAATGAGCAGAAT
LeIF E         CTGCCTCTGGGCTGTGATCTGCCTCAGGCCCACAGCCTGGGTAACAGGAGGGGCCTTCATACTCCTGACACAAATGAGGAGAAT
LeIF F  TCAGCTACAAATCCATCTGTTCTCTGGGCTGTGATCTGCCTCAGACCCACAGCCTGGGTAATAGGAGGGCCTTGATACTCCTGGCACAAATGGGAAGAAT
LeIF G
LeIF H  TCAGCTGCAAGTCAAGCTGCTCTCTGGGCTGTAATCTGTCTCAAACCCACAGCCTGAATAACAGGAGGACTTTGATGCTCATGGCACAAATGAGGAGAAT 160              180              200              220              240
                  ,                ,                ,                ,                ,
LeIF A  CTCTCTTTTCTCCTGCTTGAAGGACAGACATGACTTTGGATTTCCC CAGGAGGAGTTT   GGCAACCAGTTCCAAAAGGCTGAAACCATCCCTGTCCT
LeIF B  CTCTCCTTTCTCCTGCCTGAAGGACAGACATGACTTTGAATTCCCC CAGGAGGAGTTTTGATGATAAACAGTTCCAGAAGGCTCAAGCCATCTCTGTCCT
LeIF C  CTCTCCTTTTCTCCTGCCTGAAGGACAGACATGATTTCCGAATCCCC CAGGAGGAGTTTGATGGCAACCAGTTCCAGAAGGCTCAAGCCATCTCTGTCCT
LeIF D  CTCTCCTTCCTCCTGTCTGATGGACAGACATGACTTTGGATTTCCC CAGGAGGAGTTTGATGGCAACCAGTTCCAGAAGGCTCAAGCCATCTCTGTCCT
LeIF E  CTCTCCTTTTTCTTACCTGAAGGACAGACATGACTTTGATTTCCATCATCAGGTGTTTCATGGCAACCACTTCCAGAAGGTTCAAGCTATCTTCCTTTT
LeIF F  CTCTCCTTTCTCCTGCCTGAAGGACAGACATGACTTTGGATTCCCC  CAAGAGGAGTTTGATGGCAACCAGTTCCAGAAGGCTCAAGCCATCTCTGTCCT
LeIF G                         CATGACTTTGGATTTCCT CAGGAGGAGTTTGATGGCAACCAGTTCCAGAAGGCTCAAGCCATCTCTGTCCT
LeIF H  CTCTCCTTTCTCCTGCCTGAAGGACAGACATGACTTTGAATTTCCC CAGGAGGAATTTGATGGCAACCAGTTCCAGAAAGCTCAAGCCATCTCTGTCCT 260              280              300              320              340
                  ,                ,                ,                ,                ,
LeIF A  CCATGAGATGATCCAGCAGATCTTCAATCTCTTCAGCACAAAGGACTCATCTGCTGCTTGGGATGAGACCCTCCTAGACAAATTCTACACTGAACTCTAC
LeIF B  CCATGAGATGATCCAGCAGACCTTCAACCTCTTCAGCACAAAGGACTCATCTGCTGCTTTTGGATGAGACCCTTCTAGATGAATTCTACATCGAACTTGAC
LeIF C  CCATGAGATGATCCAGCAGACCTTCAATCTCTTCAGCACAGAGGACTTCATCTGCTGCTTGGGAACAGGAGCCTCCTAGAAAAATTTCCACTGAACTTTAC
LeIF D  CCATGAGCTGATCCAGCAGATCTTCAACCTCTTTACCACAAAAGATTCATCTGCTGCTTGGGATGAGGACCTCCTAGACAAATTCTGCACCGAACTCTAC
LeIF E  CCATGAGATGATGCAGCAGACCTTCAACCTCTTCAGCACAAAAGGACTCATCTGATACTTGGGATGAGACCCTTTAGACAACCCTTTCTACACTGAACTTTAC
LeIF F  CCATGAGATGATCCAGCAGACCTTCAATCTCTTCAGCACAAAGGACTCATCTGCTACTTGGGAACAGAGCCTCCTGAAAAATTTTCCACTGAACTTAAC
LeIF G  CCATGATGATGCAGCAGACCTTCAATCTCTTCAGCACAAAGACTCATCTGCTACTTGGGATGAGACACTTCTAGACAAATTCTACACTGAACTTTAC
LeIF H  CCATGAGATGATGCAGCAGACCTTCAATCTCTTCAGCACAAAGAACTCATCTGCTGCTTGGGATGAGACCCTCCTAGAAAAATTCTACATTGAACTTTTC 360              380              400              420              440
                  ,                ,                ,                ,                ,
LeIF A  CAGCAGCTGAATGACCTGGAAGCCTGTGTGATACAGGGGGTGGGGTGACAGAGACTCCCCTGATGAAGGAGGACTCCATTCTGGCTGTGAGGAAATACT
LeIF B  CAGCAGCTGAATGACCTGGAAGTCCTGTGTGATCAGGAAGTGGGGGTGATAGAGTCTCCCCTGATGTACGAGGACTCCATCCTGGCTGTGAGGAAATACT
LeIF C  CAGCAACTGAATGACCTGGAAGCATGTGTGATACAGGAGGTTGGGGTGGAAGAGACTCCCCTGATGAATGAGGACTCCATCCTGGCTGTGAGGAAATACT
LeIF D  CAGCAGCTGAATGACTTGGAAGCCTGTGTGATGCAGGAGGAGAGGGTGGGACAAACTCCCCTGATGAATGAGGACTCCATCTTGGCTGTGAGGAAATACT
LeIF E  CAGCAGCTGAATGACCTGGAAGCCTGTGTGATGTAGAAGGTTGGAGTGGAAGAGACTCCCCTGAGGAATGTGGACTCCATCCTGGCTGTGAGAAAATACT
LeIF F  CAGCAGCTGAATGACATGGAAGCCTGCGTGATACAGGAGGTTGGGGTGGACAAACTCCCCTGATGAATGAGGACTCCATCCTTGGCTGTGAAGAAATACT
LeIF G  CAGCAGCTGAATGACCTGGAAGCCTGTATGATGCAGGAGGTTGGAGTGGAAGACACTCCTCTGATGAATGTGGACTCTATCCTGACTGTGAGAAAATACT
LeIF H  CAGCAAATGAATGACCTGGAAGCCCTGTGTGATACAGGAGGTTGGGGTGGAAGAGACTCCCCTGATGAATGAGGACTCCATCCTGGCTGTGAAGAAATACT 460              480              500              520              540
                  ,                ,                ,                ,                ,
LeIF A  TCCAAAGAATCACTCTCTATCTGAAAGAGAAGAAATACAGCCCCTTGTGCCTGGGAGGTTGTCAGAGCAGAAATCATGAGATCTTTTTCTTTGTCAACAAA
LeIF B  TCCAAAGAATCACTCTATATCTGACAGAGAAGAAATACAGCCTTCTTGTGCCTGGGAGGTTGTCAGAGCAGAAATCATGAGATCCTTCTCTTTTATCAATCAA
LeIF C  TCCAAAGAATCACTCTTTATCTAATAGAGAGGAAATACAGCCCCTTGTGCCTGGGAGGTTGTCAGAGCAGAAATCATGAGATCCCTCTCTGTTTTCAACAAA
LeIF D  TCCGAAGAATCACTCTCTATCTGACAGAGAAGAAATACAGCCCCTTGTGCCTGGGAGGTTGTCAGAGCAGAAATCATGAGATCCCTCTCTTTATCAACAAA
LeIF E  TTCAAGAAGAATCACTTTATCTGACAAAGAAGAAGTATAGCCCCTTGTTCCTGGGAGGTCGTCAGAGCAGAAATCATGAGATCCTTCTCTTTTGAACCAA
LeIF F  TCCAAAGAATCACTCTTTATCTGACAGAGAAGAAATACAGCCCCTTGTGCCTTGGGAGGTTGTCAGAGCAGAAATCATGAGATCCTTCTCTTTTATCAAAAAT
LeIF G  TTCAAGAATCACCCTCTATCTGACAGAGAAGAAATACAGCCCTTGTGCATGGGAGGTTGTCAGAGCAGAAATCATGAGATCCTTCTCTTTTATCAGCAAA
LeIF H  TCCAAAGAATCACTCTTTATCTGATGGAGAAGAAATACAGCCCCTTGTGCCTGGGAGGTTGTCAGAGCAGAAATCATGAGATCCTTCTCTTTTTCAACAAA 560              580              600              620              640
                  ,                ,                ,                ,                ,
LeIF A  CTTGCAAGAAAGTTTAAGAAGTAAGGAATGAAAACTGGTTCAACATGGAAATGATTTTCATTGATTCGTATGCCAGCTCACCTTTTATGATCTGCCATT
LeIF B  CTTGCAAAAAAGATTGAACAGTAAGGAATGACCTGGTACAACACGGAAATGATTCTCATAGACTAATACAGCAGTCTACACTTTGACAAGTTGTGCTC
LeIF C  CTTGCAAAAAAGATTAAGGAGGAAGGATTGAAAACTGGTTCAACATGGCAATGATCCTGATTGACTAATACATTATCTCACACTTTCATGAGTTCTTCCA
LeIF D  CTTGCAAAAAAGATTAAGGAGGAAGGAATAATATCTGGTCCAACATGAAAACAATTCTTATTGACTCATACACCAGGTCACCTTTCATGAATTCTGTCA
LeIF E  CTTGCAGGAAAAGATTAAGGAGGAAGGAATGAAAACTGGTTCAACATGGAAATGAGAAACATTTCCATGATTAATACATCATCTCACACATTCATGAATTC
LeIF F  TTTTCAAGAAACATTAAGGAGGAAGGAATGAAACCGTTTCAACATGAAATGATCTGTATTGACTAATACACCGCCACCTTCTATGACTTCTGCCAT
LeIF G  CTTGCAAGAAAGATTAAGGAGGAAGGAATGAAAACTGGTTCAACATCGAAATGATTCTCATTGACTACTAGTACACCATTTCACACTTCTTGAGTTCTGCCGT
LeIF H  CTTGCAAAAAAGATTAAGGAGGAAGGATGAAAACTGGTTCATCATGGAAATGATTCTCATTGACTAATACATCATCTCACACTTTCATGTTCTTCCATT 660              680              700              720              740
                  ,                ,                ,                ,                ,
LeIF A  TCAAAGACTCATGTTTCTGCTATGACCATGACACGATTTAAATCTTTTCAAATGTTTTTAGGAGTATTAATCAACATTGTATTCAGCTCTTAAGGCACTA
LeIF B  TTTCAAAGACCCTTGTTTCTGCCAAAACCATGCTATGAATTGAATCAAATGTGTCAAGTGTTTTCAGGAGTGTTAAGCACATCCTGTTCAGCTGTATGG
LeIF C  TTTCAAGACTCACTTCTATAACCACGACGCGTTGAATCAAAATTTTCAAATGTTTTCAAATGAATGTGAAGGACAGTGTAAAGAGCTTGTGCAGGCACTAG
LeIF D  TTTCAAAGACTCTCACCCCTGCTATAACTATGACCATGCTGATAAACTCGATTATCTATTTAAATATTTATTTAACTATTCATAAGATTTAAATTATTTT
LeIF E  TGCCATTTCATTTTTGCTATATGCATGACATGAGTTGAATCAAAATTTTAAAATGTTTTCAGGAAGTGTAAGCAAACATCATGTTTACCTGTCGACAGGCA
LeIF F  TTCAAAGACTCATTTCTCCTATAACGACCGCATGAGTTGAATCAAAATTTTCAGATCCTTTTCAGGAGTGTAAGGAAACATCATGTTTACCTGTGCAGGGA
LeIF G  TCAAATATTAATTTCTGCTATATCCATGACTTGAGTTGAATCAAAATTTTCAAACGTTTCACACGTGTTAAGCAACACTTCTTTAGCTCCACAGGGACA
LeIF H  TCAAAGACTCACTTCTATAACCACCACAAGTTGAATCAAAATTTCCAAATGTTTTCAGGAGTGTTAAGAAGCATCGTGTTTACCTGTGCAGGCACTAGTC 760              780              800              820              840
                  ,                ,                ,                ,                ,
LeIF A  GTCCCTTACAGAGGACCATGCTGACTGATCCATTATCTATTTAAATATTTTTAAAATATTATTTATTTAACTATTTATAAAACAACTTATTTTTGTTCAT
LeIF B  GCACTAGTCCCTTACAGATGACCATGCTGATGGATCTATTCATCTATTTATTTAATTCTTTATTTAGTTAACTATAGGGACTTAAATTAGTTTTGTT
LeIF C  TCCTTTACAGATGACCATTCTGATGTCTCTGTTCATCTTTGTTTAAATATTTATTTAATTATTTTTTAAAATTTATGTAATATCATGACTGCTTTACAT
LeIF D  TGTTCATATAACGTCATGTGCACCTTTACACTGTGGTTAGTGTAATAAAACATGTTCCTTATATTTACTC-poly(A)
LeIF E  CTAGTTCCTTACGGATGATCATGCTGATGGATCTGTTTATCTATTTGTCTAAATAATTATTAACTATTTATAATATTTAAAATCTTCTTTTCATGTATC
LeIF F  CTAGTCCTTTACAGATGACCATGCTGATAGATCTAATTATCTATCTATTGAAATATTTATTTTATTAGATTTAAATTATTTTTGTCCATGTAATATT
LeIF G  AAATCTTTACAGATGATCATGCCAATCTATCTATTCTATCTATTCATCTATCTGTCTGTCTTCTATCTAATCTATTTAAATATTTATTTATTTATAAGAT
LeIF H  TCAAAGACTCACTTCTATAACCACCACAAGTTGAATCAAAATTTCCAAATGTTTTCAGGAGTGTTAAGAAGCATCGTGTTTACCTGTGCAGGCACTAGTC 860              880              900              920              940
                  ,                ,                ,                ,                ,
LeIF A  ATTACGTCATGTGCACCTTTGCACAGTGGTTAATGTAATAAAAATATGTCTTTGTATTTGGT-poly(A)
LeIF B  CATATATTATATGTGAACTTTTACATTGTGAATTGTGTAACAAAAACATGTTCTTATATTTATTATTTTGCCATGTTTATTAAATTTTTACTATGAAAA
LeIF C  TGTGGTTAATGTAACAATATATGTTCTTCATATTTAGCCAATATATTAATTTCCTTTTTCATTAAATTTTTTACTATAC-poly(A)
LeIF E  ATGTATTTTTACTTTGTGGTTAATATAACAACACATGTTCTTTATATTTAGTCAATATTACTTTGCTTTTTTACTATGG-poly(A)
LeIF F  ATGTGACTTTTACATTGTGTATATCAAAATATGTTAATCTAATATTTAGTCAATATATTTTCTTTTTTATTAATTTTTACTATTAAAACTTCTTAT
LeIF G  TTAAATTATTTTAAACTTATGCTTGTTCAGGTAATAATTAACATCCACCTTACTTTGTGGCTAATATAATAAAAATATGTCTTTATGTTTTGTC-poly(A)
LeIF H  TGAGTACCTTTACATTGTGGTTAATGTAACAAATATGTTCTTCATATTTAGCCAATATATTAATTTCCTTTTTCATTAAATTTTTACTAT-poly(A)

960              980             1000
                  ,                ,                ,
LeIF B  AATTCTTTATTTATTCTTTAAAATTGAACTGCAACCCATGAATTGTGCAAACTGATTAAAGAATGGATGGT-poly(A)
LeIF F  ATTATTTGGTTATTCTTTAATAAAGAAATTCCAAGCCC-poly(A)
```

```
           1                          10                          20                          30
LeIF A   CYS ASP LEU PRO GLN THR HIS SER LEU GLY SER ARG ARG THR LEU MET LEU LEU ALA GLN MET ARG LYS ILE SER LEU PHE SER CYS LEU LYS ASP ARG HIS
LeIF D                       GLU            ASP ASN                                                 SER ARG                     PRO SER     MET 40                          50                          60
LeIF A   ASP PHE GLY PHE PRO GLN GLU GLU PHE .... GLY ASN GLN PHE GLN LYS ALA GLU THR ILE PRO VAL LEU HIS GLU MET ILE GLN GLN ILE PHE ASN LEU PHE
                                                                                                                         BglII
LeIF D                                       ASP                              PRO ALA             SER                       LEU 70                          80                      PvuII  90                         100
LeIF A   SER THR LYS ASP SER SER ALA ALA TRP ASP GLU THR LEU LEU ASP LYS PHE TYR THR GLU LEU TYR GLN GLN LEU ASN ASP LEU GLU ALA CYS VAL ILE GLN
LeIF D   THR                                 ASP                                                 CYS                                           MET 110                         120                         130
LeIF A   GLY VAL GLY VAL THR GLU THR PRO LEU MET LYS GLU ASP SER ILE LEU ALA VAL ARG LYS TYR PHE GLN ARG ILE THR LEU TYR LEU LYS GLU LYS LYS TYR
LeIF D   GLU GLU ARG     GLY                         ASN VAL               LYS                 ARG                             THR 140                         150                         160                 166
LeIF A   SER PRO CYS ALA TRP GLU VAL VAL ARG ALA GLU ILE MET ARG SER PHE SER LEU SER THR ASN LEU GLN GLU SER LEU ARG SER LYS GLU
LeIF D                                               LEU                                                 ARG     ARG         ARG
```

```
A                                                                                                            GTATGTTCCCTA
H                                                                                                            GTATGTTCCCTA
I                                                                                                            GTATGTTCCTTA
J                                                                                                            GTATGTTCACTA
C                                                                                                            GTATGTTCACTA

A    TTTAAGGC-TAGGCACAAAGCAAGGTCTTCAGAGAACCTGGAGCCTAAGGTTTAGGCTCACCCATT-TCAACCAGTCTAGCAGCATCTGCAACATCTACA
H    TTTAAGGC-TAGGCACAAAGCAAGGTCTTCAGAGAACCTGGAGCCTAAGGTTTAGGCTCACCCATT-TCAACCAGTCTAGCAGCATCTGCAACATCTACA
I    TTTAAGACCTATGCACAGAGCAAGGTCTTCAGAAAACCTACAACCCAAGGTTCAGTGTTACCCCTCATCAACCAGCCCAGCAGCATCTTCAGGGTTCCCA
J    TTTAAGGCCTATGCACAGAGCAAAGTCTTCAGAAAACCTAGAGGCCAAAGTTCAAGGTTACCCATC-TCAAGTAGCCTAGCAACATTTGCAACATCCCA-
C    TTTAAGACCTATGCACAGAGCAAAGTCTCCAGAAAACCTAGAGGCCACGGTTCAA-GTTACCCACC-TCAGGTAGCCTAGTGATATTTGCAAAATCCCA-

+1                                                                                             100
A    ATGGCCTTGACCTTTGCTTTACTGGTGGCCCTCCTGGTGCTCAGCTGCAAGTCAAGCTGCTCTGTGGGCTGTGATCTGCCTCAAACCCACAGCCTGGGTA
H    ATGGCATTGCCCTTTGCTTTAATGATGGCCCTGGTGGTGCTCAGCTGCAAGTCAAGCTGCTCTCTGGGCTGTAATCTGTCTCAAACCCACAGCCTGAATA
I    ATGGCCCTGTCCTTTTCTTTACTGATGGCCGTGCTGGTGCTCAGCTACAAATCCATCTGTTCTCTAGGCTGTGATCTGCCTCAGACCCACAGCCTGGGTA
J    ATGGCCCGGTCCTTTTCTTTACTGATGGTCGTGCTGGTACTCAGCTACAAATCCATCTGCTCTCTGGGCTGTGATCTGCCTCAGACCCACAGCCTGCGTA
C    ATGGCCCTGTCCTTTTCTTTACTTATGGCCGTGCTGGTGCTCAGCTACAAATCCATCTGATCTCTGGGCTGTGATCTGCCTCAGACCCACACCCTGCGTA

200
A    GCAGGAGGACCTTGATGCTCCTGGCACAGATGAGGAGAATCTCTCTTTTCTCCTGCTTGAAGGACAGACATGACTTTGGATTTCCCCAGGAGGAGTTT--
H    ACAGGAGGACTTTGATGCTCATGGCACAAATGAGGAGAATCTCTCCTTTCTCCTGCCTGAAGGACAGACATGACTTTGAATTTCCCCAGGAGGAATTTGA
I    ATAGGAGGGCCTTGATACTCCTGGCACAAATGGGAAGAATCTCTCCTTTCTCCTGCCTGAAGGACAGACCTGACTTTGGACTTCCCCAGGAGGAGTTTGA
J    ATAGGAGGGCCTTGATACTCCTGGCACAAATGGGAAGAATCTCTCCTTTCTCCTGCTTGAAGGACAGACATGAATTCAGATTCCCAGAGGAGGAGTTTGA
C    ATAGGAGGGCCTTGATACTCCTGGGACAAATGGGAAGAATCTCTCCTTTCTCCTGCCTGAAGGACAGACATGATTTCCGAATCCCCCAGGAGGAGTTTGA

300
A    -GGCAACCAGTTCCAAAAGGCTGAAACCATCCCTGTCCTCCATGAGATGATCCAGCAGATCTTCAATCTCTTCAGCACAAAGGACTCATCTGCTGCTTGG
H    TGGCAACCAGTTCCAGAAAGCTCAAGCCATCTCTGTCCTCCATGAGATGATGCAGCAGACCTTCAATCTCTTCAGCACAAAGAACTCATCTGCTGCTTGG
I    TGGCAACCAGTTCCAGAAGACTCAAGCCATCTCTGTCCTCCATGAGATGATCCAGCAGACCTTCAATCTCTTCAGCACAGAGGACTCATCTGCTGCTTGG
J    TGGCCACCAGTTCCAGAAGACTCAAGCCATCTCTGTCCTCCATGAGATGATCCAGCAGACCTTCAATCTCTTCAGCACAGAGGACTCATCTGCTGCTTGG
C    TGGCAACCAGTTCCAGAAGGCTCAAGCCATCTCTGTCCTCCATGAGATGATCCAGCAGACCTTCAATCTCTTCAGCACAGAGGACTCATCTGCTGCTTGG

400
A    GATGAGACCCTCCTAGACAAATTCTACACTGAACTCTACCAGCAGCTGAATGACCTGGAAGCCTGTGTGATACAGGGGGTGGGGTGACAGAGACTCCCC
H    GATGAGACCCTCCTAGAAAAATTCTACATTGAACTTTTCCAGCAAATGAATGACCTGGAAGCCTGTGTGATACAGGAGGTTGGGGTGGAAGAGACTCCCC
I    GAACAGAGCCTCCTAGAAAAATTTTCCACTGAACTTTACCAGCAACTGAATAACCTGGAAGCATGTGTGATACAGGAGGTTGGGATGGAAGAGACTCCCC
J    GAACAGAGCCTCCTAGAAAAATTTTCCACTGAACTTTACCAGCAACTGAATGACCTGGAAGCATGTGTGATACAGGAGGTTGGGGTGGAAGAGACTCCCC
C    GAACAGAGCCTCCTAGAAAAATTTTCCACTGAAATTTACCAGCAACTGAATGACCTGGAAGCATGTGTGATACAGGAGGTTGGGGTGGAAGAGACTCCCC

500
A    TGATGAAGGAGGACTCCATTCTGGCTGTGAGGAAATACTTCCAAAGAATCACTCTCTATCTGAAAGAGAAGAAATACAGCCCTTGTGCCTGGGAGGTTGT
H    TGATGAATGAGGACTCCATCCTGGCTGTGAAGAAATACTTCCAAAGAATCACTCTTTATCTGATGGAGAAGAAATACAGCCCTTGTGCCTGGGAGGTTGT
I    TGATGAATGAGGACTCCATCCTGGCTGTGAGGAAATACTTCCAAAGAATCACTCTTTATCTAACAGAGAAGAAATACAGCCCTTCAGCCTGGGAGGTTGT
J    TGATGAATGAGGACTTCATCCTGGCTGTGAGGAAATACTTCCAAAGAATCACTCTTTATCTAATGGAGAAGAAATACAGCCCTTGTGCCTGGGAGGTTGT
C    TGATGAATGAGGACTCCATCCTGGCTGTGAGGAAATACTTCCAAAGAATCACTCTTTATCTAATAGAGAGGAAATACAGCCCTTGTGCCTGGGAGGTTGT

600
A    CAGAGCAGAAATCATGAGATCTTTTTCTTTGTCAACAAACTTGCAAGAAAGTTTAAGAAGTAAGGAATGAAAACTGGTTCAACATGGAAATGATTTTCAT
H    CAGAGCAGAAATCATGAGATCCCTCTCTTTTTCAACAAACTTGCAAAAAAGATTAAGGAGGAAGGATTGAAAAGTGGTTCATCATGGAAATGATTCTCAT
I    CAGAGCAGAAATCATGAGATCTCTCTCTTTTTCAACAAACTTGCAAAAAATATTAAGGAGGAAGGATTGAAAACTGGTTCAACATGGCAATGATCCTGAT
J    CAGAGCAGAAATCATGAGATCCTTCTCTTTTTCAACAAACTTGAAAAAAGGATTAAGGAGGAAGGATTGAAAACTGGTTCATCATGGAAATGATTCTCAT
C    CAGAGCAGAAATCATGAGATCCCTCTCGTTTTCAACAAACTTGCAAAAAAGATTAAGGAGGAAGGATTGAAAACTGGTTCAACATGGCAATGATCCTGAT

700
A    TGATTCGTATGCCAGCTCACCTTTTTATGATCTGCCATTTCAAAGACTCATGTTTCTGCTATGACCATGACACGATTTAAATCTTTTCAAATGTTTTTAG
H    TGACTAATACATCATCTCACACTTTCATGAGTTCTTCCATTTCAAAGACTCACTTCTCCTATAACCACCACAAGTTGAATCAAAATTTTTCAAATGTTTTC
I    TGACTAATACATTATCTCACACTTTCATGAGTTCCTCCATTTCAAAGACTCACTTCTATAACCACCACGAGTTGAATCAAAATTTTCAAATGTTTTCAGC
J    TGACTAATGCATCATCTCACACTTTCATGAGTTCTTCCATTTCAAAGACTCACTTCTATAACCACCACAAGTTGAATCAAAATTTTCCAAATGTTTTCAGG
C    TGACTAATACATTATCTCACACTTTCATGAGTTCTTCCATTTCAAAGACTCACTTCTATAACCACGACGTGTTGAATCAAAATTTTCAAATGTTTTCAGC

800
A    GAGTATTAATCAACATTGTATTCAGCTCTTAAGGCACTAGTCCCTTACAGAGGACCATGCTGACTGATCCATTATCTATTTAAATATTTTTAAAATATTA
H    AGGAGTGTAAAGAAGCATCATGTATACCTGTGCAGGCACTAGTCCTTTACAGATGACCATGCTGATGTCTCCTTTCATCTATTTATTTAAATATTTATTT
I    AGTGTAAAGAAGCGTCGTGTATACCTGTGCAGGCACTAGTACTTTACAGATGACCATGCTGATGTCTCTGTTCATCTATTTATTTAAATATTTATTTAAT
J    AGTGTTAAGAAGCATCGTGTTTACCTGTGCAGGCACTAGTCCTTTACAGATGACCATTCTGATGTCTCCTTTCATCTATTTATTTAAATATTTATTTATT
C    AGTGTAAAGAAGTGTCGTGTATACCTGTGCAGGCACTAGTCCTTTACAGATGACCATTCTGATGTCTCTGTTCATCTTTTGTTTAAATATTTATTTAATT

900
A    TTTATTTAACTATTTATAAAACAACTTATTTTTGTTCATATTTATGTCATGTGCACCTTTGCACAGTGGTTAATGTAATAAAATGTGTTCTTTGTATTTGG
H    ATTTAACTATTTTTATTATTTAAATTATTTTTTATGTTAATATCATGTGTACCTTTACATTGTGGTTAATATAACAAATATGTTCTTCATATTTAGCCAA
I    TATTTTTAAGATTTAAATTATTTTTTTATGTAATATCATGTGTACCTTTACATTGTGGTAATGTAACAATATATGTTCTTCATATTTAGCCAATATATT
J    TAACTATTTTTATTATTTAAATTATTTTTTATGTAATATCATATGTACCTTTACATTGTGGTTAATGTAACAAATATGTTCTTCATATTTAGCCAATATA
C    ATTTTTAAAATTTATGTAATATCATGAGTCGCTTTACATTGTGGTTAATGTAACAATATATGTTCTTCATATTTAGCCAATATATTAATTTCCTTTTTCA 1,000
A    TAAAATTTATTTTGTGTTGTTCATTGAACTTTTGCTATGGAACTTTTGTACTTGTTTATTCTTTAAAATGAAATTCCAAGCCTAATTGTGCAACCTGATTA
H    TATATTTCCTTTTTCATTAAATTTTACTATACAAAATTTCTGTGTTTGGTATTT
I    AATTTCCTTTTTCATTAAATTTTTACTATACAAAATTTCTTGAGTTTGTTTATTCTTAAGAATAAAATGTCGAGGCTGACTTTACAACCTGACTTAAAAA
J    TTAATTTCCTTTTT CATTAAATTTTTACTATACAAAATTTCTTGTGTTTGTTTATTTTTAAGATTAAATGCCAAGCCTGACTGTATAACCTGACTTAA
C    TTAAATTTTTACTATACAAAATTTCTTGTGTTTGTTTATTCTTTAAGATAAAATGCCAAGGCTGACTTTACAACCTGACTTAAAAATAGATGATTTAATT
```

FIG. 9.

HYBRID HUMAN LEUKOCYTE INTERFERONS

CROSS REFERENCE TO RELATED APPLICATIONS

This is a continuation in part of applications Ser. No. 237,388, filed Feb. 23, 1981, U.S. Pat. No. 4,414,150 issued Nov. 8, 1983 and Ser. No. 205,579, filed Nov. 10, 1980, now abandoned.

This application is in part related in subject matter to U.S. patent applications of David V. Goeddel and Sidney Pestka, Ser. No. 205,578, filed Nov. 10, 1980 and Ser. No. 184,909 filed Sept. 8, 1980 and Ser. No. 164,986, filed July 1, 1980. The disclosure of each of these foregoing related applications is incorporated herein by reference to illuminate the background of the invention and to provide additional detail relative to the practice thereof.

FIELD OF THE INVENTION

This invention relates to the microbial production, via recombinant DNA technology, of hybrid leukocyte interferons for use in the treatment of viral and neoplastic diseases, and to the means and end products of such production.

BACKGROUND OF THE INVENTION

Relatively homogeneous leukocyte interferons have been derived from normal or leukemic donors' leukocytes. These interferons are a family of proteins characterized by a potent ability to confer a virus-resistant state in their target cells. In addition, interferon can act to inhibit cell proliferation and modulate immune response. These properties have prompted the clinical use of interferon as a therapeutic agent for the treatment of viral infections and malignancies.

More recently, recombinant DNA technology has been employed to occasion the microbial production of a number of different leukocyte interferons whose amino acid sequences exhibit on the order of 70 percent homology, one relative to another, all as disclosed in the aforementioned related U.S. patent applications of Goeddel and Pestka and in the manuscript of David V. Goeddel et al. entitled "The Structures of Eight Distinct Cloned Human Leukocyte Interferon cDNAs", published in *Nature* 290, 20 (1981) and incorporated herein by this reference. The manner in which genes encoding amino acid sequences of various leukocyte interferons designated, inter alia, LeIF A,B,C,D,F,G and H, respectively, are obtained from the cell line KG-1 described in Koeffler, H.P. and Golde, D. W. *Science* 200, 1153–1154 (1978) is disclosed in the aforementioned related applications of Goeddel and Pestka. The cell line KG-1 has been deposited with the American type culture collection, ATCC Accession Number CRL 8031. Such genes, appropriately deployed in plasmidic vehicles for bacterial expression, may be employed to transform host bacteria, preferably *E. coli* K-12 strain 294, American type culture collection Accession No. 31446, deposited Oct. 28, 1978.

The workhorse of recombinant DNA technology is the plasmid, a non-chromosomal loop of double-stranded DNA found in bacteria and other microbes, oftentimes in multiple copies per cell. Included in the information encoded in the plasmid DNA is that required to reproduce the plasmid in daughter cells (i.e., a "replicon") and ordinarily, one or more selection characteristics such as, in the case of bacteria, resistance to antibiotics which permit clones of the host cell containing the plasmid of interest to be recognized and preferentially grown in selective media. The utility of plasmids lies in the fact that they can be specifically cleaved by one or another restriction endonuclease or "restriction enzyme", each of which recognizes a different site on the plasmidic DNA. Thereafter heterologous genes or gene fragments may be inserted into the plasmid by endwise joining at the cleavage site or at reconstructed ends adjacent to the cleavage site. DNA recombination is performed outside the cell, but the resulting "recombinant" plasmid can be introduced into it by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting expression vehicle can be used to actually produce the polypeptide sequence for which the inserted gene codes, a process referred to as expression.

Expression is initiated in a region known as the promoter which is recognized by and bound by RNA polymerase. In some cases, as in the tryptophan or "trp" promoter preferred in the practice of the present invention, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a nucleotide triplet or "codon" within what may for present purposes be referred to as the "structural gene", i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other bacterial protein.

BRIEF SUMMARY OF THE INVENTION

Nucleotide sequence studies of genes encoding the various leukocyte interferons reveals a degree of commonality amongst various of them with regard to the presence and location of cleavage sites recognized by particular restriction endonucleases. According to the present invention, advantage may be taken of this commonality to form, by DNA recombination, novel hybrid genes useful in the microbial production of hybrid leukocyte interferons which may be expected to exhibit in greater or lesser degree the antiviral and other properties of interferons encoded by the parental genes. In preferred embodiments of the invention, such hybrid leukocyte interferons may exhibit enhanced activity relative to those encoded by the parental genes.

The parental leukocyte interferon genes, encoding the family of leukocyte interferon proteins contemplated herein, exhibit natural allelic variations from individual to individual. These variations may be demonstrated by (an) amino acid difference(s) in the overall protein sequence or by deletions, substitutions, insertions, inversions or additions of (an) amino acid(s) in said sequence. For each parental leukocyte interferon hereof, labelled LeIF A, LeIF B . . . LeIF J, etc., such allelic variations are included within the scope of the label or term defining such, and thus, this invention.

The manner in which these and other objects and advantages of the invention are obtained will become further apparent from the detailed description which follows and from the accompanying drawings in which:

BRIEF DESCRIPTION OF THE DRAWINGS

FIG. 1 depicts nucleotide sequences of the coding regions of 8 leukocyte interferon ("LeIF") complementary DNA ("cDNA") clones. Of these, one, correspondingly designated LeIF E, is an apparent "pseudogene" encoding no active leukocyte interferon while another, designated LeIF G, contains less than the full sequence for the corresponding interferon species. The ATG translational initiation codon and the termination triplet for each LeIF is underlined.

FIG. 3 is a comparison of the eight LeIF protein sequences predicted from the nucleotide sequences. The one letter abbreviations recommended by the IUPAC-IUB Commission on Biochemical Nomenclature are used: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine. The numbers refer to amino acid position (S refers to signal peptide). The dash in the 165 amino acid LeIF A sequence at position 44 is introduced to align the LeIF A sequence with the 166 amino acid sequences of the other LeIFs. The LeIF E sequence was determined by ignoring the extra nucleotide (position 187 of FIG. 1) in its coding region. The asterisks indicate in-phase termination codons. Amino acids common to all LeIFs (excluding the pseudogene LeIF E) are also shown. The underlined residues are amino acids which are also present in human fibroblast interferon.

With reference to FIG. 1, nucleotides +1 to 69 correspond to S1 to S23 amino acids of FIG. 3. Codon TGT (nucleotides 70 to 72) of FIG. 1 corresponds to cysteine (C, amino acid 1) of FIG. 3. In FIG. 3, the Pvu II restriction endonuclease cleavage site occurs between the codons for amino acids 92 and 93 in LeIF A,B,D,F and G, i.e., between nucleotides 346 and 347, of FIG. 1.

FIG. 4 compares the amino acid sequences of mature leukocyte interferons A and D, a deletion of amino acid 44 in LeIF A being indicated by dashes. Only those LeIF D amino acids which differ from corresponding amino acids of LeIF A are depicted: the amino acid sequence of LeIF D is otherwise identical of LeIF A. FIG. 4 also indicates the relative position on the corresponding gene of Bgl II and Pvu II restriction endonuclease cleavage sites employed in forming preferred hybrid leukocyte genes of the invention.

FIG. 9 provides the DNA sequences of five LeIF proteins hereof, including types I and J.

DESCRIPTION OF THE PREFERRED EMBODIMENTS

Microorganisms Employed

Figure 2:
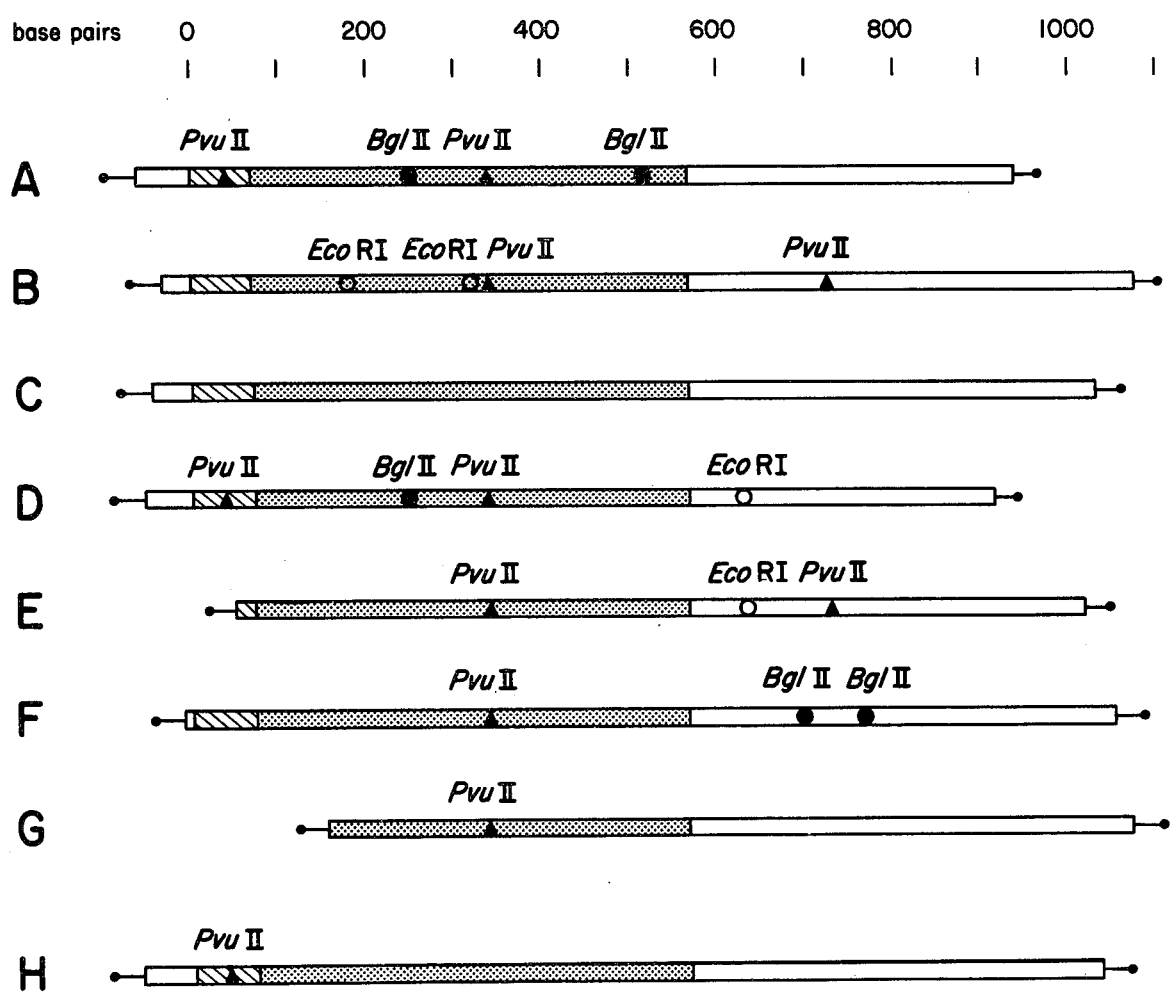
FIG. 2 depicts restriction endonuclease maps of eight types of LeIF cloned cDNAs (A through H). Plasmids containing the clones were constructed by the dC:dG tailing method, Goeddel, D.V. et al. *Nature* 287, 411–416 (1980). Therefore the cDNA inserts can be excised using Pst I, i.e., each end of each insert is a Pst I restriction endonuclease cleavage site. The lines at the end of each cDNA insert represent the flanking homopolymeric dC:dG tails. The positions of Pvu II, Eco RI and Bgl II restriction sites are indicated. Shaded regions of the Figure represent the coding sequences of mature LeIFs; the cross-hatched regions indicate signal peptide coding sequences; and the open regions show 3' and 5' noncoding sequences.

The work described involved use of two microorganisms: *E. coli* x1776, as described in U.S. Pat. No. 4,190,495, and *E. coli* K-12 strain 294 (end A, thi−, hsr−, hsm$_k$+), as described in British Patent Publication No. 2055382A. Each has been deposited with the American Type Culture Collection, ATCC Accession Nos. 31537 and 31446, deposited July 3, 1979 and Oct. 28, 1978, respectively. All recombinant DNA work was performed in compliance with applicable guidelines of the National Institutes of Health.

The invention, in its most preferred embodiments, is described with reference to *E. coli*, including not only strains *E. coli*×1776 and *E. coli* K-12 strain 294, defined above, but also other known *E. coli* strains such as *E. coli* B, or other microbial strains many of which are deposited and (potentially) available from recognized microorganism depository institutions, such as the American Type Culture Collection (ATCC)—cf. the ATCC catalogue listing. See also German Offenlegungsschrift No. 2644432. These other microorganisms include, for example, Bacilli such as Bacillus subtilis and other enterobacteriaceae among which can be mentioned as examples Salmonella typhimurium and Serratia marcesans, utilizing plasmids that can replicate and express heterologous gene sequences therein. Yeast, such as Saccharomyces cerevisiae, may also be employed to advantage as host organism in the preparation of the interferon proteins hereof by expression of genes coding therefor under the control of a yeast promoter. (See the copending U.S. patent application of Hitzeman et al., U.S. Ser. No. 237,913, filed Feb. 25, 1981, assignee Genentech, Inc. et al., which is incorporated herein by reference.)

The LeIF hybrids are prepared, in accordance with the present invention, by taking advantage of restriction endonuclease cleavage sites commonly located within the individual parental genes and each end thereof in conjunction with the same sites in carrier expression plasmids (vectors). For example, the large (~3900 bp) fragment of a Xba I to Pst I digest of the pLeIF A trp 25 expression plasmid can be ligated with Xba I to Pvu II and Pvu II to Pst I digest fragments of the various LeIF parental genes to provide expression plasmids operable to obtain the corresponding hybrid LeIF.

Each LeIF expression plasmid was constructed independently with digest fragments isolated from various LeIF plasmids, e.g., pLeIF A trp 25, pLeIF B trp 7, pLeIF C trp 35, pLeIF D trp 11, pLeIF F trp 1, pLeIF G, pLeIF H, and pLeIF I, etc. whose construction and description are described in the aforementioned applications of Goeddel and Pestka, and in Goeddel et al., *Nature* 287, 411 (1980) or from pBR322, whose construction and description is described by Bolivar et al., *Gene* 2, 95 (1977). In certain of these plasmids, "trp" designates a tryptophan promoter-operator system most preferred for bacterial expression, as described in the copending, commonly owned U.S. patent application of Dennis G. Kleid et al., Serial No. 06/133,296, filed Mar. 24, 1980, which is hereby incorporated by reference.

Direct Expression of a First Mature Leukocyte Interferon

The procedure followed to express Le-IF A directly as a mature interferon polypeptide involved the combination of synthetic (N-terminal) and complementary DNAs.

A Sau 3a restriction endonuclease site is conveniently located between codons 1 and 2 of Le-IF A. Two synthetic deoxyoligonucleotides were designed which incorporate an ATG trinslational initiation codon, restore the codon for amino acid 1 (cysteine), and create an Eco RI sticky end. These oligomers were ligated to a 34 b.p. Sau 3a-Ava II fragment of pL31. The resulting 45 b.p. product was ligated to two additional DNA fragments to construct an 865 base pair synthetic-natural hybrid gene which codes for Le-IF A and which is bounded by Eco Ri and Pst I restriction sites. This gene was inserted into pBR322 between the Eco RI and Pst I sites to give the plasmid pLe-IF A1.

Plasmid pGM1 carries the *E. coli* tryptophan operon containing the deletion Δle1413 (G. F. Miozzari, et al., (1978) *J. Bacteriology* 133, 1457–1466)) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. The plasmid, 20 μg, was digested with the restriction enzyme Pvu II which cleaves the plasmid at five sites. The gene fragments were next combined with EcoRI linkers (consisting of a self complementary oligonucleotide of the sequence: pCATGAATTCATG) providing an EcoRI cleavage site for a later cloning into a plasmid containing an EcoRI site. The 20 μg of DNA fragments obtained from pGM1 were treated with 10 units T4 DNA ligase in the presence of 200 pico moles of the 5'-phosphorylated synthetic oligonucleotide pCATGAATTCATG and in 20μl T4 DNA ligase buffer (20 mM tris, pH 7.6, 0.5 mM ATP, 10 mM MgCl2, 5 mM dithreitol) at 4' C. overnight. The solution was then heated 10 minutes at 70° C. to halt ligation. The linkers were cleaved by EcoRI digestion and the fragments, now with EcoRI ends were separated using 5 percent polyacrylamide gel electrophoresis (hereinafter "PAGE") and the three largest fragments isolated from the gel by first staining with ethidium bromide, locating the fragments with ultraviolet light, and cutting from the gel the portions of interest. Each gel fragment, with 300 microliters 0.1×TBE, was placed in a dialysis bag and subjected to electrophoresis at 100 v for one hour in 0.1×TBE buffer (TBE buffer contains: 10.8 gm tris base, 5.5 gm boric acid, 0.09 gm Na2EDTA in 1 liter H2O). The aqueous solution was collected from the dialysis bag, phenol extracted, chloroform extracted and made 0.2M sodium chloride, and the DNA recovered in water after ethanol precipitation. The trp promoter-operator-containing gene with EcoRI sticky ends was identified in the procedure next described, which entails the insertion of fragments into a tetracycline sensitive plasmid which, upon promoter-operator insertion, becomes tetracycline resistant.

Plasmid pBRH1 (R. I. Rodriguez, et al., Nucleic Acids Research 6, 3267–3287 [1979]) expresses ampicillin resistance and contains the gene for tetracycline resistance but, there being no associated promoter, does not express that resistance. The plasmid is accordingly tetracycline sensitive. By introducing a promoter-operator system in the EcoRI site, the plasmid can be made tetracycline resistant.

pBRH1 was digested with EcoRI and the enzyme removed by phenol extraction followed by chloroform extraction and recovered in water after ethanol precipitation. The resulting DNA molecule was, in separate reaction mixtures, combined with each of the three DNA fragments obtained above and ligated with T4 DNA ligase as previously described. The DNA present in the reaction mixture was used to transform competent *E. coli* K-12 strain 294, K. Backman et al., Proc Nat'l Acad Sci USA 73, 4174–4198 [1976]) by standard techniques (V. Hershfield et al., Proc Nat'l Acad Sci USA 71, 3455–3459 [1974]) and the bacteria plated on LB plates containing 20 μg/ml ampicillin and 5 μg/ml tetracycline. Several tetracycline-resistant colonies were selected, plasmid DNA isolated and the presence of the desired fragment confirmed by restriction enzyme analysis. The resulting plasmid is designated pBRHtrp.

An EcoRI and BamHI digestion product of the viral genome of hepatitis B was obtained by conventional means and cloned into the EcoRI and BamHI sites of plasmid pGH6 (D. V. Goeddel et al., Nature 281, 544 [1979]) to form the plasmid pHS32. Plasmid pHS32 was cleaved with XbaI, phenol extracted, chloroform extracted and ethanol precipitated. It was then treated with 1 μl *E. coli* polymerase I, Klenow fragment (Boehringer-Mannheim) in 30 μl polymerase buffer (50 mM potassium phosphate pH 7.4, 7 mM MgCl2, 1 mM β-mercaptoethanol) containing 0.1 mM dTTP and 0.1 mM dCTP for 30 minutes at 0° C. then 2 hr. at 37° C. This treatment causes 2 of the 4 nucleotides complementary to the 5' protruding end of the XbaI cleavage site to be filled in:

| 5' | CTAGA— | 5' | CTAGA— |
|----|--------|----|--------|
| 3' | T—     | 3' | TCT—   |

Two nucleotides, dC and dT, were incorporated giving an end with two 5' protruding nucleotides. This linear residue of plasmid pHS32 (after phenol and chloroform extraction and recovery in water after ethanol precipitation) was cleaved with EcoRI. The large plasmid fragment was separated from the smaller EcoRI-XbaI fragment by PAGE and isolated after electroelution. This DNA fragment from pHS32 (0.2 μg), was ligated, under conditions similar to those described above, to the EcoRI-Taq I fragment of the tryptophan operon (~0.01 μg), derived from pBRHtrp.

In the process of ligating the fragment from pHS32 to the Eco RI-Taq I fragment, as described above, the Taq I protruding end is ligated to the XbaI remaining protruding end even though it is not completely Watson-Crick base-paired:

A portion of this ligation reaction mixture was transformed into *E. coli* 294 cells, heat treated and plated on LB plates containing ampicillin. Twenty-four colonies were selected, grown in 3 ml LB media, and plasmid isolated. Six of these were found to have the XbaI site regenerated via E. coli catalyzed DNA repair and replication:

| —TCTAGA— | —TCTAGA— |
|---|---|
| —AGCTCT— | —AGATCT— |

These plasmids were also found to cleave both with EcoRI and HpaI and to give the expected restriction fragments. One plasmid, designated pTrp 14, was used for expression of heterologous polypeptides, as next discussed.

The plasmid pHGH 107 (D. V. Goeddel et al, *Nature*, 281, 544, 1979) contains a gene for human growth hormone made up of 23 amino acid codons produced from synthetic DNA fragments and 163 amino acid codons obtained from complementary DNA produced via reverse transcription of human growth hormone messenger RNA. This gene, though it lacks the codons of the "pre" sequence of human growth hormone, does contain an ATG translation initiation codon. The gene was isolated from 10 μg pHGH 107 after treatment with EcoRI followed by *E. coli* polymerase I Klenow fragment and dTTP and dATP as described above. Following phenol and chloroform extraction and ethanol precipitation the plasmid was treated with BamHI.

The human growth hormone ("HGH") gene-containing fragment was isolated by PAGE followed by electroelution. The resulting DNA fragment also contains the first 350 nucleotides of the tetracycline resistance structural gene, but lacks the tetracyline promoter-operator system so that, when subsequently cloned into an expression plasmid, plasmids containing the insert can be located by the restoration of tetracycline resistance. Because the EcoRI end of the fragment has been filled in by the Klenow polymerase I procedure, the fragment has one blunt and one sticky end, ensuring proper orientation when later inserted into an expression plasmid.

The expression plasmid pTrp14 was next prepared to receive the HGH gene-containing fragment prepared above. Thus, pTrp14 was XbaI digested and the resulting sticky ends filled in with the Klenow polymerase I procedure employing dATP, dTTP, dGTP and dCTP. After phenol and chloroform extraction and ethanol precipitation the resulting DNA was treated with BamHI and the resulting large plasmid fragment isolated by PAGE and electroelution. The pTrp14-derived fragment had one blunt and one sticky end, permitting recombination in proper orientation with the HGH gene containing fragment previously described.

The HGH gene fragment and the pTrp14 ΔXba-BamHI fragment were combined and ligated together under conditions similar to those described above. The filled in XbaI and EcoRI ends ligated together by blunt end ligation to recreate both the XbaI and the EcoRI site:

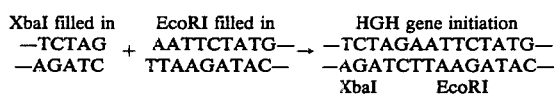

This construction also recreates the tetracycline resistance gene. Since the plasmid pHGH 107 expresses tetracycline resistance from a promoter lying upstream from the HGH gene (the lac promoter), this construction, designated pHGH 207, permits expression of the gene for tetracycline resistance under the control of the tryptophan promoter-operator. Thus the ligation mixture was transformed into *E. coli* 294 and colonies selected on LB plates containing 5 μg/ml tetracycline.

Plasmid pHGH207 was Eco RI digested and the trp promoter containing a 300 b.p. Eco RI fragment recovered by PAGE followed by electroelution. The 300 b.p. Eco RI fragment contains the *E. coli* trp promoter, operator, and trp leader ribosome binding site but lacks an ATG sequence for initiation of translation. This DNA fragment was cloned into the Eco RI site of pLeIF A.

The trp fragment just referred to is an analog of the *E. coli* tryptophan operon from which the so-called trp attenuator has been deleted, to controllably heighten expression levels. Expression plasmids containing the modified trp regulon can be grown to predetermined levels in nutrient media containing additive tryptophan in quantities sufficient to repress the promoter-operator system, then be deprived of tryptophan so as to derepress the system and occasion the expression of the intended product (36). See Kleid et al., Supra.

More particularly, 250 μg of plasmid pL31 were digested with Pst I and the 1000 b.p. insert isolated by gel electrophoresis on a 6 polyacrylamide gel. Approximately 40 μg of insert was electroeluted from the gel and divided into 3 aliquots for further digestion: (a) A 16 μg sample of this fragment was partially digested with 40 units of Bgl II for 45' at 37° C. and the reaction mixture purified on a 6 polyacrylamide gel. Approximately 2 μg of the desired 670 b.p. fragment were recovered. (b) Another sample (8 μg) of the 1000 b.p. Pst I insert was restricted with Ava II and Bgl II. One μg of the indicated 150 b.p. fragment was recovered after gel electrophoresis. (c) 16 μg of the 1000 b.p. piece was treated with Sau 3a and Ava II. After electrophoresis on a 10 polyacrylamide gel, approximately 0.25 μg (~10 pmole) of the 34 b.p. fragment was recovered. The two indicated deoxyoligonucleotides, 5'-dAATTCATGTGT (fragment 1) and 5'-d GATCACACATG (fragment 2) were synthesized by the phosphotriester procedure (24). Fragment 2 was phosphorylated as follows. 200 μl (~40 pmole) of (γ=P) ATP (Amersham, 5000 Ci/mmole) was dried down and resuspended in 30 μl of 60 mM Tris-HCl (pH8), 10 mM MgCl₂, 15 mM β-merceptoethanol, containing 100 pmoles of DNA fragment and 2 units of T4 polynucleotide kinase. After 15 minutes at 37° C., 1 μl of 10 mM ATP was added and the reaction allowed to proceed another 15 minutes. The mixture was then heated at 70° C. for 15 minutes, combined with 100 pmole of 5'-OH fragment 1 and 10 pmole of the 34 b.p. Sau 3a-Ava II fragment. Ligation was performed for 5 hours at 4° C. in 50 μl of 20 mM Tris-HCl (pH 7.5) 10 mM Mg Cl₂, 10 mM dithiothreitol, 0.5 mM ATP and 10 units T4 DNA ligase. The mixture was electrophoresed on a 6 polyacrylamide gel and the 45 b.p. product recovered by electroelution. 860,000 Cerenkov cpm were recovered (~30 ng, 1 pmole), combined with 0.5 μg (5 pmoles) of the 150 b.p. Ava II-Bgl II fragment and 1 μg (2 pmoles) of the 670 b.p. Bgl II-Pst I fragment. The ligation was performed at 20° C. for 16 hours using 20 units of T4 DNA ligase. The ligase was inactivated by heating to 65° C. for 10 minutes. The mixture was then digested with Eco RI and Pst I to eliminate polymers of the gene. The mixture was purified by 6 percent polyacrylamide gel electrophoresis. 36,000 cpm (~0.04 pmole, 20 ng) of 865 b.p. product were isolated. One-half (10 ng) of this was ligated into pBR322 (0.3 μg) between the Eco RI and Pst I sites. Transformation of *E. coli* 294 gave 70 tetracycline resistant, ampicillin sensitive transformants. Plasmid DNA isolated from 18 of these transformants was digested with Eco RI and Pst I. 16 of the 18 plasmids had an Eco RI-Pst I fragment 865 b.p. in length. One μg of one of these, pLe-IF A1, was digested with Eco RI and ligated to a 300 b.p. Eco RI fragment (0.1 μg) containing the *E. coli* trp promoter and trp leader ribosome binding site, prepared as described above. Transformants containing the trp promoter were identified using a ³²P-trp probe in conjunction with the Grunstein-Hogness colony screening procedure—Grunstein et al., *Proc. Natl. Acad. Sci.* (USA) 72, 3961 (1975). An asymetrically located Xba I site in the trp fragment allowed determination of recombinants in which the trp promoter was oriented in the direction of the Le-IF A gene.

Extracts were prepared for IF assay as follows. One ml cultures were grown in L broth containing 5 μg/ml tetracycline to an $A_{550}$ of about 1.0, then diluted into 25 ml of M9 media containing 5 μg/ml tetracycline. 10 ml samples were harvested by centrifugation when $A_{550}$ reached 1.0 and cell pellets were suspended in 1 ml of 15 percent sucrose, 50 mM Tris-HCl (pH 8.0), 50 mM EDTA. One mg of lysozyme was added and, after 5 minutes at 0° C., cells were disrupted by sonication. The samples were centrifuged 10 minutes at 15,000 rpm in a Sorvall SM-24 rotor. Interferon activity in the supernatants was determined by comparison with Le-IF standards by the cytopathic effect (CPE) inhibition assay. To determine the number of IF molecules per cell a Le-IF specific activity of $4 \times 10^8$ units/mg was used—Rubinstein et al., *Proc. Natl. Acad. Sci.* (USA) 76, 640 (1979).

Clone pLe-IF A trp 25, in which the trp promoter was inserted in the desired orientation, gives high levels of activity (as high as $2.5 \times 10^8$ units per liter). The IF produced by *E. coli* K-12 strain 294/pLe-IF A trp 25 behaves like authentic human Le-IF; it is stable to treatment at pH2 and is neutralized by rabbit anti-human leukocyte antibodies. The interferon has an apparent molecular weight of approximately 20,000.

Isolation of cDNAs for Additional Leukocyte Interferons

DNA from the fully characterized Le-IF A cDNA-containing plasmid was excised with Pst I, isolated electrophoretically, and labelled by a published procedure, Taylor et al., *Biochem. Biophys. Acta.* 442, 324 (1976), with ³²P. The resulting radioactively labelled DNA was used as a probe to screen additional *E. coli* 294 transformants, obtained identically as those in Part D, by an in situ colony screening procedure, Grunstein et al., *Supra*. Colonies were isolated which hybridized in varying amounts to the probe. Plasmid DNA from these colonies and the ten hybridizing colonies referred to in Part I above was isolated by Pst cutting and characterized by three different methods. First, these Pst fragments were characterized by their restriction endonuclease digestion patterns with the enzymes Bgl II, Pvu II, and Eco RI. This analysis allowed the classification of at least eight different types (Le-IF A, Le-IF B, Le-IF C, Le-IF D, Le-IF E, Le-IF F, Le-IF G and Le-IF H), which approximates the location of various restriction cuts relative to the by-now known presequence and coding sequence of Le-IF A. One of these, Le-IF D, is believed to be identical to that reported by Nagata et al., *Nature* 284, 316 (1980).

Secondly, certain of the DNAs were tested by a published hybridization selection assay, Cleveland et al., *Cell* 20, 95 (1980), for the ability to selectively remove Le-IF mRNA from poly-A containing KG-1 cell RNA. Le-IF A, B, C and F were positive by this assay. Third, the latter Pst fragments were inserted in an expression plasmid, *E. coli* 294 transformed with the plasmid, and the fragments expressed. The expression products, believed to have been preinterferons, were all positive by CPE assay for interferon activity, albeit marginally active in the case of the Le-IF-F fragment. In addition to the foregoing, all of the Le-IF types described have been sequenced.

Second Mature Leukocyte Interferon

The sequence of the isolated fragment comprising the gene for mature Le-IF-B shows the first fourteen nucleotides of types A and B to be identical. We accordingly proposed to isolate a fragment from pLe-IF A25 bearing the trp-promoter-operator, ribosome binding site and the start of the Le-IF (A=B) gene, and combine this with the remaining portion of the B sequence in an expression plasmid.

To obtain the approximately 950 b.p. Sau 3a to Pst I fragment from the sequence shown in FIG. 7a several steps were necessary because of the presence of one or more intervening Sau 3a restriction sites, i.e.:

1. The following fragments were isolated:
   (a) 110b b.p. from Sau 3a to Eco RI;
   (b) 132 b.p. from Eco RI to Xba;
   (c) >700 b.p. from Xba to Pst.
2. Fragments (1a) and (1b) were ligated and cut with Xba and Bgl II to preclude self-polymerization through Sau 3a and Xba end terminals (the relevant Sau 3a site was within a Bgl II site; Bgl II cuts to leave a Sau 3a sticky end). A 242 b.p. fragment was isolated.
3. The product of (2) and (1c) were ligated and cut with Pst I and Bgl II, again to prevent self-polymerization. An approximate 950 b.p. fragment, Sau 3a to Pst I of FIG. 7a, was isolated. This fragment comprised that portion of the Le-IF B gene not common to Le-IF A.

4. An approximate 300 b.p. fragment (Hind III to Sau 3a) comprising the trp promoter-operator, ribosome binding site, ATG start signal and cysteine codon of Le-IF A was isolated from pLe-IF A25.
5. An approximately 3600 b.p. fragment Pst I to Hind III was isolated from pBr 322. This comprised the replicon and encoded tetracycline but not ampicillin resistance.
6. The fragments obtained in steps 3, 4 and 5 were triple-ligated and the resulting plasmid transformed into *E. coli* K-12 strain 294.

Transformants were miniscreened, Birnboim et al., *Nucleic Acid* Research 7, 1513 (1979), and plasmid samples were digested with Eco RI. Digests yielded three fragments characteristic of:

(1) The Eco RI-Eco RI trp promoter fragment; (2) The internal Eco RI to Eco RI fragment of pL4; and (3) protein translational start signal to Eco RI fragment of pL4.

In CPE assay, bacterial extracts from clones made in the foregoing fashion typically assay at about $10 \times 10^6$ units interferon activity per liter at $A_{550}=1$. One representative clone prepared in this manner is 294/pLIF B trp 7.

Further Mature Leukocyte Interferons

Additional full-length gene fragments that comprise other Le-IF types may be tailored and placed in expression vehicles for expression as in the case of Le-IF A. Complete sequencing by conventional means will reveal whether a restriction site lies sufficiently near the first amino acid codon of the mature interferon type as to permit convenient resort to the approach employing the elimination of the presequence by restriction cutting and replacement of codons for the N-terminal amino acids lost in presequence elimination by ligation of a synthetic DNA fragment, as described above. Failing that, the procedure described in Kleid et al., Supra may be employed. Briefly, this entails cleaving the presequence-containing fragment precisely before the point at which the codon for the first amino acid of the mature polypeptide begins, by:

1. converting the double stranded DNA to single-stranded DNA in a region surrounding that point;
2. hybridizing to the single-stranded region formed in step (a) a complementary primer length of single-stranded DNA, the 5' end of the primer lying opposite the nucleotide adjoining the intended cleavage site;
3. restoring that portion of the second strand eliminated in step 1 which lies in the 3' direction from the primer by reaction with DNA polymerase in the presence of adenine, thymine, guanine and cytosine-containing deoxynucleotide triphosphates; and
4. digesting the remaining single-stranded length of DNA which protrudes beyond the intended cleavage point.

A short length of synthetic DNA terminating, at the 3' end of the coding strand, with the translation start signal ATG can then be ligated by, e.g., blunt-end ligation to the resulting tailored gene for the mature interferons and the gene inserted into an expression plasmid and brought under the control of a promoter and its associated ribosome binding site.

In a manner similar to that employed above, gene fragments encoding Le-IF-C and Le-IF-D were appropriately configured for direct bacterial expression. The expression strategy for these additional leukocyte interferons included, in each case, resort to the approximately 300 b.p. fragment (Hind III to Sau 3a) comprising the trp promoter-operator, ribosome binding site, ATG start signal and cysteine codon of Le-IF A from pLe-IF A25. To this were combined gene fragments from the additional interferon genes encoding their respective amino acid sequences beyond the initial cysteine common to all. Each resulting plasmid was used to transform *E. coli* K-12 strain 294. Ligations to form the respective genes were as follows:

Le IF-C

Isolate the following fragments from pLe IF-C:
(a) 35 b.p. from Sau 3a to Sau 96
(b) >900 b.p. Sau 96 to Pst
(c) Isolate an approximate 300 b.p. fragment (Hind III-Sau 3a) from pLe IF A-25 as in part N (4) supra.
(d) Isolate the approximately 3600 b.p. fragment of part N (5) supra.
Construction:
(1) Ligate (a) and (c). Cleave with Bgl II, Hind III and isolate the approximately 335 b.p. product.
(2) Triple ligate (1)+(b)+(d) and transform *E. coli* with the resulting plasmid.

A representative clone made in this manner is *E. coli* K-12 strain 294/pLe IF C trp 35.

Le-IF D

Isolate from pLe IF-D:
(a) 35 b.p. from Sau 3a to Ava II
(b) 150 b.p. from Ava II to Bgl II
(c) approx. 700 b.p. from Bgl II to Pst
Isolate from pLe IF A25:
(d) 300 b.p. from Hind III to Sau 3a
Isolate from PBr 322:
(e) approx. 3600 b.p. from Hind III to Pst
Construction:
(1) ligate (a)+(b), cut with Bgl II and purify a 185 b.p. product (1).
(2) ligate (1)+(d), cut with Hind III, Bgl II, and purify the approx. 500 b.p. product (2).
(3) ligate (2)+(c)+(e) and transform *E. coli* with the resulting plasmid.

A representative clone made in this manner is *E. coli* K-12 strain 294/pLeIF D trp 11.

Le-IF F

The Le-IF F containing fragment may be tailored for direct expression through reassembly made convenient by the complete homology of amino acids 1–13 of Le-IF B and Le-IF F. A trp promoter-containing fragment (a) with appropriately configured ends is obtained from pHGH 207, described above, via Pst I and Xba I digestion followed by isolation of the ca. 1050 b.p. fragment. A second fragment (b) is obtained as the larger of the fragments resulting from Pst I and Bgl II digestion of the plasmid pHKY 10, a derivative of pBR322 which contains a Bgl II site between the tetracycline resistance promoter and structural gene. Fragment (a) contains approximately half the gene encoding amplicillin resistance; fragment (b) contains the remainder of that gene and the entire gene for tetracycline resistance save for the associated promoter. Fragments (a) and (b) are combined via T4 ligase and the product treated with Xba I and Bgl II to eliminate dimerization, forming a fragment (c) comprising the trp promoter-operator and genes for tetracycline and ampicillin resistance.

A fragment (d) of approximately 580 b.p. is obtained by Ava II and Bgl II digestion of pLe IF-F. This comprises codons for amino acids 14–166 of Le-IF F.

A fragment (e) (49 b.p.) is obtained by Xba I and Ava II digestion of pLe-IF B. Fragment (e) encodes amino acids 1–13 of Le-IF F.

Fragments (c), (d) and (e) are triple ligated in the presence of T4 ligase. The cohesive ends of the respective fragments are such that the composite plasmid circularizes correctly, bringing the tetracycline resistance gene under the control of the trp promoter-operator along with the gene for mature Le-IF F, such that bacteria transformed with the desired plasmid may be selected on tetracycline-containing plates. A representative clone prepared in this manner is E. coli K-12 strain 294/pLeIF F trp 1.

Le-IF H

The complete Le-IF H gene may be configured for expression as a mature leukocyte interferon as follows:

1. Plasmid pLe-IF H is subjected to Hae II and Rsa I digestion with isolation of the 816 base pair fragment extending from the signal peptide amino acid 10 to the 3′ noncoding region.

2. The fragment is denatured and subjected to repair synthesis with Klenow fragment, Klenow et al., Proc. Natl. Acad. Sci. (USA) 65, 168 (1970), employing the synthetic deoxyribooligonucleotide primer 5′-dATG TGT AAT CTG TCT. This general procedure is also described by Goeddel et al., U.S. Ser. No. 190,799, filed Sept. 25, 1980.

3. The resulting product is cleaved with Sau 3a and a 452 base pair ("bp") fragment representing amino acids 1 to 150 isolated.

4. Sau 3a and Pst I digestion of pLeIF H and isolation of the resulting 500 b.p. fragment yields a gene encoding amino acids 150 through the end of the coding sequence.

5. Fragments isolated in steps (3) and (4) are ligated to form a fragment:

| 1 | | 166 | |
|---|---|---|---|
| met cys | | asp stop | |
| ATG TGT | | GAT TGA | Pst I |
| | Sau 3a | | | encoding the 166 amino acids of Le-IF H.

6. pLeIF A trp 25 is digested with Xba I, blunt-ended with DNA polymerase I and the product digested with Pst I. The large resulting fragment may be isolated and ligated with the product of step (5) to form an expression plasmid capable, upon transformation of E. coli K-12 strain 294 or other host bacteria, of expressing mature Le-IF H.

LeIF-I

The phage λ Charon 4A recombinant library of the human genome constructed by Lawn et al., Cell 15, 1157 (1978), was screened for leukocyte interferon genes by procedures described by Lawn et al., Supra and Maniatis et al., Cell 15, 687 (1978). A radioactive LeIF probe derived from the cDNA clone LeIF A (Goeddel et al., Nature 287, 411 (1980), was used to screen approximately 500,000 plaques. Six LeIF genome clones were obtained in this screening. Following rescreening and plaque purification, one of these clones, λHLeIF2, was selected for further analysis.

Using the method described above, other probes can be used to advantage to isolate additional LeIF clones from the human genome. These, in turn, can be employed to produce additional leukoctye interferon proteins in accordance with this invention.

1. The 2000 base pair Eco RI fragment of the genomic clone (λHLeIF2) was subcloned into pBR325 at the Eco RI site. The resulting plasmid LeIF I was cleaved with Eco RI and the 2000 base pair fragment isolated. The deoxyoligonucleotide dAATTCTGCAG (an Eco RI>Pst I convertor) was ligated to the 2000 base pair Eco RI fragment and the resulting product cleaved with Pst I to give a 2000 base pair fragment containing Pst I ends. This was cleaved with Sau 96 and a 1100 base pair fragment isolated which has one Pst I end and one Sau 96 end.

2. The plasmid pLeIF C trp 35 was digested with Pst I and Xba I. The large fragment was isolated.

3. The small Xba I-Pst I fragment from pLeIF C trp 35 was digested with Xba I and Sau 96. A 40 base pair Xba I-Sau 96 fragment was isolated.

4. The fragments isolated in steps (1), (2) and (3) were ligated to form the expression plasmid pLeIF I trp 1.

LeIF-J

1. The plasmid pLeIF J contains a 3.8 kilobase Hind III fragment of human genomic DNA which includes the LeIF J gene sequence. A 760 base pair Dde I-Rsa I fragment was isolated from this plasmid.

2. The plasmid pLeIF B trp 7 was cleaved with Hind III and Dde I and a 340 bp Hind III-Dde I fragment isolated.

3. The plasmid pBR322 was cleaved with Pst I, blunt ended by incubation with DNA Pol I (Klenow fragment), then digested with Hind III. The large (~3600 bp) fragment was isolated.

4. Fragments isolated in steps (1), (2) and (3) were ligated to form the expression plasmid pLeIF J trp 1.

The methods and materials employed in the following constructions were as in the foregoing description and in the aforementioned related applications of Goeddel and Pestka, mutatis mutandis. The following Table 1 provides the details for particular constructions of hybrid LeIF plasmids hereof:

TABLE 1

| LeIF Hybrid | Total Amino Acids* | Expression Plasmid (Vector) | Front Portion Fragment | Amino Acids | Back Portion Fragment | Amino Acids | Resultant Expression Plasmid |
|---|---|---|---|---|---|---|---|
| AD | 165 | a | Xba I-Pvu II of pLeIF A trp 25 (285 bp) | 1–91 | Pvu II-Pst I of pLeIF D trp 11 (~550 bp) | 93–166 | pLeIF AD trp(Pvu II) |
| DA | 166 | a | Xba I-Pvu II of pLeIF D trp 11 (288 bp) | 1–92 | Pvu II-Pst I of pLeIF A trp 25 (~550 bp) | 92–165 | pLeIF DA trp (Pvu II) |
| AD | 165 | — | Bgl II-Pst I large | 1–62 | Bgl II-Pst I | 64–166 | pLeIF AD |

TABLE 1-continued

| LeIF Hybrid | Total Amino Acids* | Expression Plasmid (Vector) | Front Portion Fragment | Amino Acids | Back Portion Fragment | Amino Acids | Resultant Expression Plasmid |
|---|---|---|---|---|---|---|---|
| | | | fragment of pLeIF A trp 25 | | of pLeIF D trp 11 (~600 bp) | | trp (Bgl II) |
| DA | 166 | — | Bgl II-Pst I large fragment pLeIF D trp 11 | 1-63 | Bgl II partial-Pst I of pLeIF A trp 25 (~700 bp) | 63-165 | pLeIF DA trp (Bgl II) |
| AB | 165 | a | Xba I-Pvu II of LeIF A trp 25 (285 bp) | 1-91 | Pvu II partial-Pst I of pLeIF B trp 7 (~750 bp) | 93-166 | pLeIF AB trp (Pvu II) |
| AF | 165 | a | Xba I-Pvu II of LeIF A trp 25 (285 bp) | 1-91 | Pvu II-Pst I of pLeIF F trp 1 (~700 bp) | 93-166 | pLeIF AF trp (Pvu II) |
| AG | 165 | a | Xba I-Pvu II of LeIF A trp 25 (285 bp) | 1-91 | Pvu II-Pst I of pLeIF G (~750 bp) | 93-166 | pLeIF AG trp (Pvu II) |
| AI | 165 | a | Xba I-Bgl II partial of pLeIF A trp 25 (~455 bp) | 1-150 | Bgl II-Pst I of LeIF I trp 1 (~650 bp) | 151-165 | pLeIF AI trp (Bgl II) |
| BA | 166 | b | Hind III-Pvu II of pLeIF B trp 7 (~630 bp) | 1-92 | Pvu II-Pst I of pLeIF A trp 25 (~550 bp) | 92-165 | pLeIF BA trp (Pvu II) |
| BD | 166 | b | Hind III-Pvu II of pLeIF B trp 7 (~630 bp) | 1-92 | Pvu II-Pst I of pLeIF D trp 11 (~550 bp) | 93-166 | pLeIF BD trp (Pvu II) |
| BF | 166 | b | Hind III-Pvu II of pLeIF B trp 7 (~630 bp) | 1-92 | Pvu II-Pst I of pLeIF F trp 1 (~700 bp) | 93-166 | pLeIF BF trp (Pvu II) |
| BG | 166 | b | Hind III-Pvu II of pLeIF B trp 7 (~630 bp) | 1-92 | Pvu II-Pst I of pLeIF G (~750 bp) | 93-166 | pLeIF BG trp (Pvu II) |
| DB | 166 | a | Xba I-Pvu II of pLeIF D trp 11 (288 bp) | 1-92 | Pvu II partial-Pst I of pLeIF B trp 7 (~750 bp) | 93-166 | pLeIF DB trp (Pvu II) |
| DF | 166 | a | Xba I-Pvu II of pLeIF D trp 11 (288 bp) | 1-92 | Pvu II-Pst I of pLeIF F trp 1 (~700 bp) | 93-166 | pLeIF DF trp (Pvu II) |
| DG | 166 | a | Xba I-Pvu II of pLeIF D trp 11 (288 bp) | 1-92 | Pvu II-Pst I of pLeIF G (~750 bp) | 93-166 | pLeIF DG trp (Pvu II) |
| FA | 166 | a | Xba I-Pvu II of pLeIF F trp 1 (288 bp) | 1-92 | Pvu II-Pst I of pLeIF A trp 25 (~550 bp) | 92-165 | pLeIF FA trp (Pvu II) |
| FB | 166 | a | Xba I-Pvu II of pLeIF F trp 1 (288 bp) | 1-92 | Pvu II partial-Pst I of pLeIF B trp 7 (~750 bp) | 93-166 | pLeIF FB trp (Pvu II) |
| FD | 166 | a | Xba I-Pvu II of pLeIF F trp 1 (288 bp) | 1-92 | Pvu II-Pst I from pLeIF D trp 11 (~550 bp) | 93-166 | pLeIF FD trp (Pvu II) |
| FG | 166 | a | Xba I-Pvu II of pLeIF F trp 1 (288 bp) | 1-92 | Pvu II-Pst I from pLeIF G (~750 bp) | 93-166 | pLeIF FG trp (Pvu II) |
| IA | 166 | a | Xba I-Bgl II of pLeIF I trp 1 (~458 bp) | 1-151 | Bgl II-Pst I of pLeIF A trp 25 (~430 bp) | 152-166 | pLeIF IA trp (Bgl II) |

*excluding N—terminal methionine
a large (~3900 bp) fragment of Xba I to Pst I digest of pLeIF A trp 25.
b large (~3600 bp) fragment of Hind III to Pst I digest of pBR322.

With further reference to Table I, the first four described hydrid LeIFs have been produced from two LeIF expression plasmids. A Bgl II site common to LeIF A and D cDNAs has been used to construct an expression plasmid pLeIF trp AD (Bgl II) which codes for the 63 amino terminal amino acids of LeIF A and the 102 carboxy terminal amino acids of LeIF D. The same site was utilized in the construction of an expression plasmid pLeIF trp DA (Bgl II) which codes for 64 amino terminal amino acids of LeIF D and 102 carboxy terminal amino acids of LeIF A. The Pvu II site has been used in the construction of two other hybrid interferon expression plasmids: 91 amino terminal amino acids of A with 74 carboxy terminal amino acids of D (pLeIF trp AD (Pvu II)) and 92 amino terminal amino acids of LeIF D with 74 carboxy terminal amino acids of LeIF A (pLeIF trp DA (Pvu II)). In summary, for:

pLeIF AD trp (Pvu II): The large (~3900 bp) fragment of an Xba I and Pst I digest of pLeIF A trp 25 was ligated with a 285 bp Xba I-Pvu II fragment of pLeIF A trp 25 and an approximately 550 bp Pvu II-Pst I fragment of pLeIF D trp 11;

pLeIF DA trp (Pvu II): The large (~3900 bp) fragment of an Xba I and Pst I digest of pLeIF A trp 25 was ligated with a 288 bp Xba I-Pvu II fragment of pLeIF D trp 11 and an approximately 550 bp Pvu II-Pst I fragment of pLeIF A trp 25;

pLeIF AD trp (Bgl II): The large fragment from a Bgl II, Pst I digest of pLeIF A trp 25 was ligated with a ~600 bp Bgl II-Pst I fragment from pLeIF D trp 11; and pLeIF DA trp (Bgl II): The large fragment from a Bgl II and Pst I digest of pLeIF D trp 11 was ligated to an approximately 700 bp fragment obtained by Pst I cleavage of pLeIF A trp 25 followed by partial Bgl II digestion.

In the fifth depicted hybrid:

pLeIF AB trp (Pvu II): The large (~3900 bp) fragment of an Xba I and Pst I digest of pLeIF A trp 25 was ligated with a 285 bp Xba I-Pvu II fragment of pLeIF A trp 25 and one approximately 750 bp Pvu II (partial)-Pst I fragment of pLeIF B trp 7.

In like manner, the other constructions depicted in Table I are so defined. As a further example, in the construction of a LeIF C and/or LeIF H portion containing hybrid, one can take advantage of common Bbv I sites occurring at about nucleotide 294 (i.e. GCTGC) of the gene sequences.

In like manner, plasmids suitable for the microbial expression of other novel hybrid leukocyte interferons may be formed by appropriate manipulation of double stranded DNA encoding all or portions of the amino acid sequences of natural occurring leukocyte interferons. Thus, a first double stranded DNA fragment is selected which encodes the amino terminal of a first, naturally occurring leukocyte interferon amino acid sequence and, proceeding therefrom in the 3' direction, a substantial portion of the amino acid sequence thereof. The fragment comprises a restriction endonuclease cleavage site positioned adjacent codons for amino acid "n" of the first leukocyte interferon, n amino acids constituting a substantial portion of the amino acid sequence of the first interferon. Cleavage with the restriction endonuclease yields a fragment comprising the amino terminal of the first interferon and codons for approximately n amino acids. A second fragment comprising all or a portion of the codons for the amino acid sequence of a second, different leukocyte interferon is selected, the fragment comprising a cleavage site for an identical restriction endonuclease positioned adjacent codons for that amino acid of the second interferon whose amino acid number (proceeding from the amino terminal of the second interferon) is approximately 166−n. Cleavage of the second fragment with that restriction endonuclease yields a product complementary to the "n" terminal portion of the digestion product of the first fragment, such that the digestion product of the second can be ligated to that of the first, reforming the restriction endonuclease recognition site and reconstituting the codon for amino acid n of the first interferon, where lost in the initial digestion. The product of the restriction endonuclease digestion of the second fragment preferably proceeds from the end resulting from cleavage in the 3' direction through nucleotides encoding the carboxy terminal of the second leukocyte interferon.

Alternatively, hybrids containing substantial portions of the amino acid sequences of more than two naturally occurring leukocyte interferons may be formed, in which event, for example, the second fragment mentioned above is additionally chosen to contain a second restriction endonuclease site downstream from the first, the second site being identical to a similarly positioned site within a fragment encoding the carboxy terminal portion of a third leukocyte interferon, etc. In the example referred to, the products of successive restriction endonuclease operations may be triple-ligated to form a hybrid gene encoding the amino terminal portion of a first interferon, the mid-range amino acid sequence of the second and the carboxy terminal portion of the third, (or, in another variation of the first, where the first and third interferons are the same).

Preferably, the first fragment mentioned above is derived from an expression plasmid, i.e., one in which codons for the amino terminal portion of the first leukocyte interferon are preceded by an ATG or other translation initiation codon and a promoter or promoter-operator system. As a result, the end product of the manipulative operations described above will be a plasmid capable of expressing the polypeptide encoded by the hybrid gene in bacteria or other microbial organisms transformed with the plasmid. Other means of configuring the hybrid gene for microbial expression will be apparent to those skilled in the art.

Figure 3:
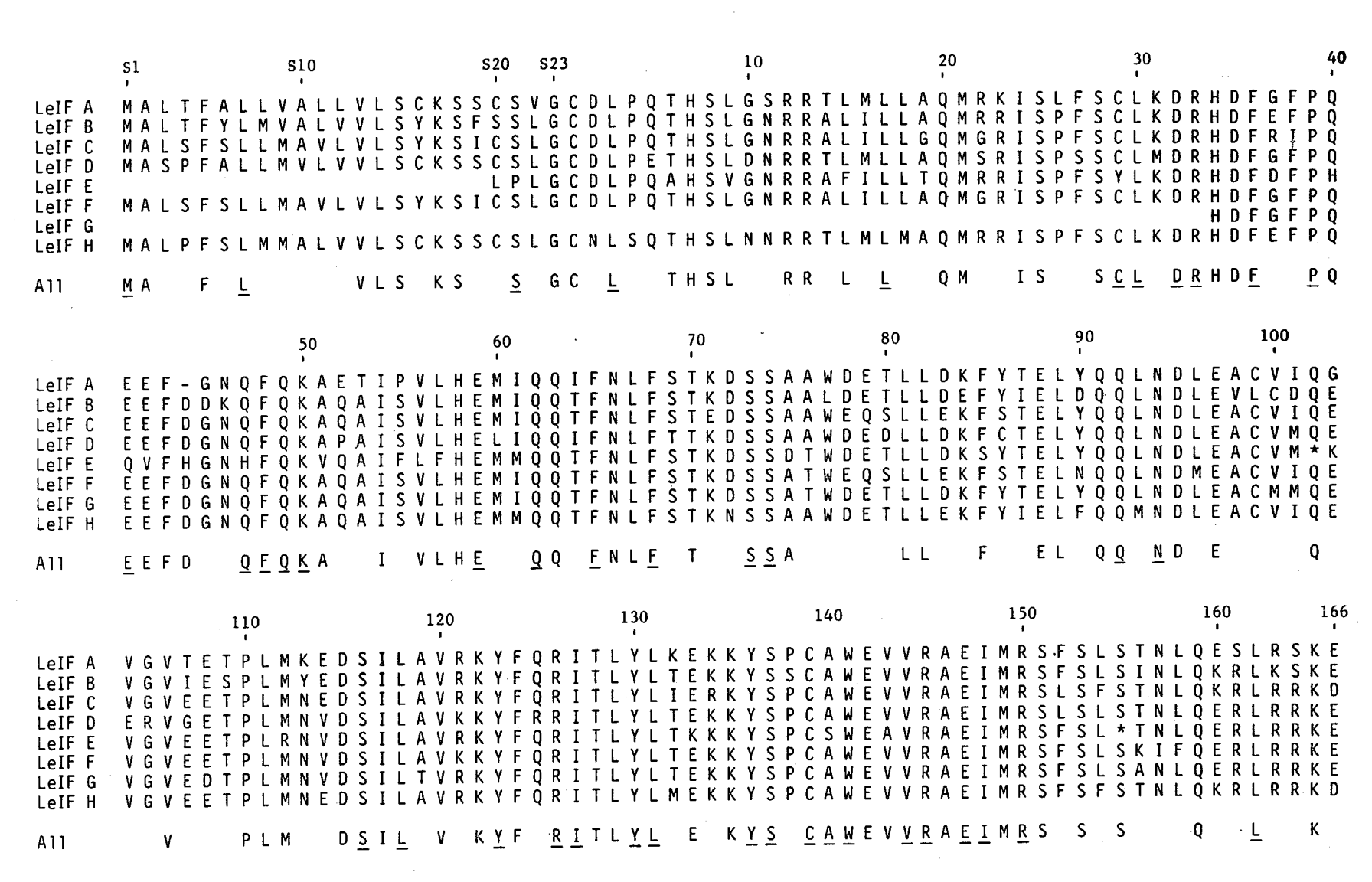

In preferred embodiments of the invention, the hybrid genes encode a novel leukocyte interferon amino acid sequence approximating 165-166 amino acids constituting a conjugate of substantial amino acid sequences drawn from two or more different leukocyte interferons selected from the group consisting of LeIF A, LeIF B, LeIF C, LeIF D, LeIF E, LeIF F, LeIF G, and LeIF H as depicted in FIG. 3. Most preferably, the novel leukocyte interferons encoded by the hybrid genes comprise the amino acids specified and positioned as indicated in the sequence "A11" of FIG. 3. The expression products of plasmids formed according to the invention may be tested for antiviral activity in conventional manner, as in the biological activity determinations next described.

DEMONSTRATION OF ANTIVIRAL ACTIVITY

E. coli K-12 strain 294 was conventionally transformed with, independently, the plasmids pLeIF trp A 25, pLeIF trp D, pLeIF trp A/D (Bgl II) and pLeIF trp D/A (Bgl II). The transformants were separately grown up in 5 ml cultures in L broth containing 5 mg/ml tetracycline to an $A_{550}$ of about 1.0, then diluted into one liter of M9 media containing 5 μg/ml tetracycline. Cells were harvested when $A_{550}$ reached 1.0 and cell pellets suspended in 10 ml of 15 percent sucrose, 50 mM tris-HCl (pH 8.0), 50 mM EDTA. 10 mg of lysozyme were added and, after 5 minutes at 0° C., cells were disrupted by sonication. The samples were centrifuged 10 minutes at 15,000 rpm in a Sorvall SM-24 rotor. Interferon activity in the supernatants was subjected to test for antiviral activity.

Further purification may be effected as in the aforementioned applications of Goeddel and Pestka.

The yields per liter of culture of these interferons, titrated on a human cell line (WISH) are shown in Table 2 from which it is apparent that LeIF-A/D activity is produced in greater amount than the other interferons. This difference could be due to greater intrinsic activity of the LeIF-A/D or to greater yield in terms of mg protein of this interferon. Because the genetic link-up was identical for all these interferons it seems most probable that LeIF-A/D essentially has greater activity than the other interferons.

TABLE 2

| YIELD OF LEUKOCYTE INTERFERONS FROM SHAKING FLASK CULTURES OF E. COLI | |
| --- | --- |
| Type interferon | Activity Yield/Liter (Units on WISH)* |
| A | $8 \times 10^7$ |
| D | $5 \times 10^6$ |
| AD (Bgl II) | $2 \times 10^8$ |
| DA (Bgl II) | $1 \times 10^6$ |

*assayed by inhibition of cytopathic effect on WISH cells with VSV as challenge.

The potency of the various interferons in a range of mammalian cell lines was determined (human, WISH; African green monkey, VERO; hamster fibroblast, BHK; rabbit kidney cells, RK-13; mouse L-929; and bovine kidney, MDBK cells). In order to compare the relative activity of the interferons their activity on various cells was calculated relative to their activity on WISH cells taken as 100. The results in Table 3 show that LeIF-A/D has very high activity in VERO and L-929 cells whereas LeIF-D/A has low activity in these cell lines. These results indicate that the combination of the N-terminal portion of LeIF-A and the C-terminal portion of LeIF-D within one molecule (LeIF-A/D) confers to the hybrid protein particular potency which is manifest in several mammalian species. Moreover, these properties are not simply the summation of the properties of the parent interferons. This is clearly seen in the case of activity on L-929 cells (Table 3) in which case neither a mixture of LeIF-A and LeIF-D nor the other hybrid, LeIF-D/A, has significant activity.

TABLE 3

TITRATION OF VARIOUS LEUKOCYTE INTERFERONS
IN CELL LINES FROM VARIOUS MAMMALIAN SPECIES

| Cell line | Leukocyte interferons* | | | | | |
|---|---|---|---|---|---|---|
| | A | D | A/D | D/A | A + D | Buffy-coat |
| WISH | 100 | 100 | 100 | 100 | 100 | 100 |
| VERO | 250 | 75 | 1,670 | 20 | 200 | 200 |
| BHK | 400 | 200 | 833 | 2,000 | 400 | 20 |
| RK-13 | 12 | 500 | 6 | N.D. | N.D. | 120 |
| L-929 | 150 | 5 | 3,300 | 2 | 10 | 0.1 |

*Interferons tested against VSV infection of the different cell lines. Activities expressed as percentage of activity observed in WISH cells.

Figure 5:
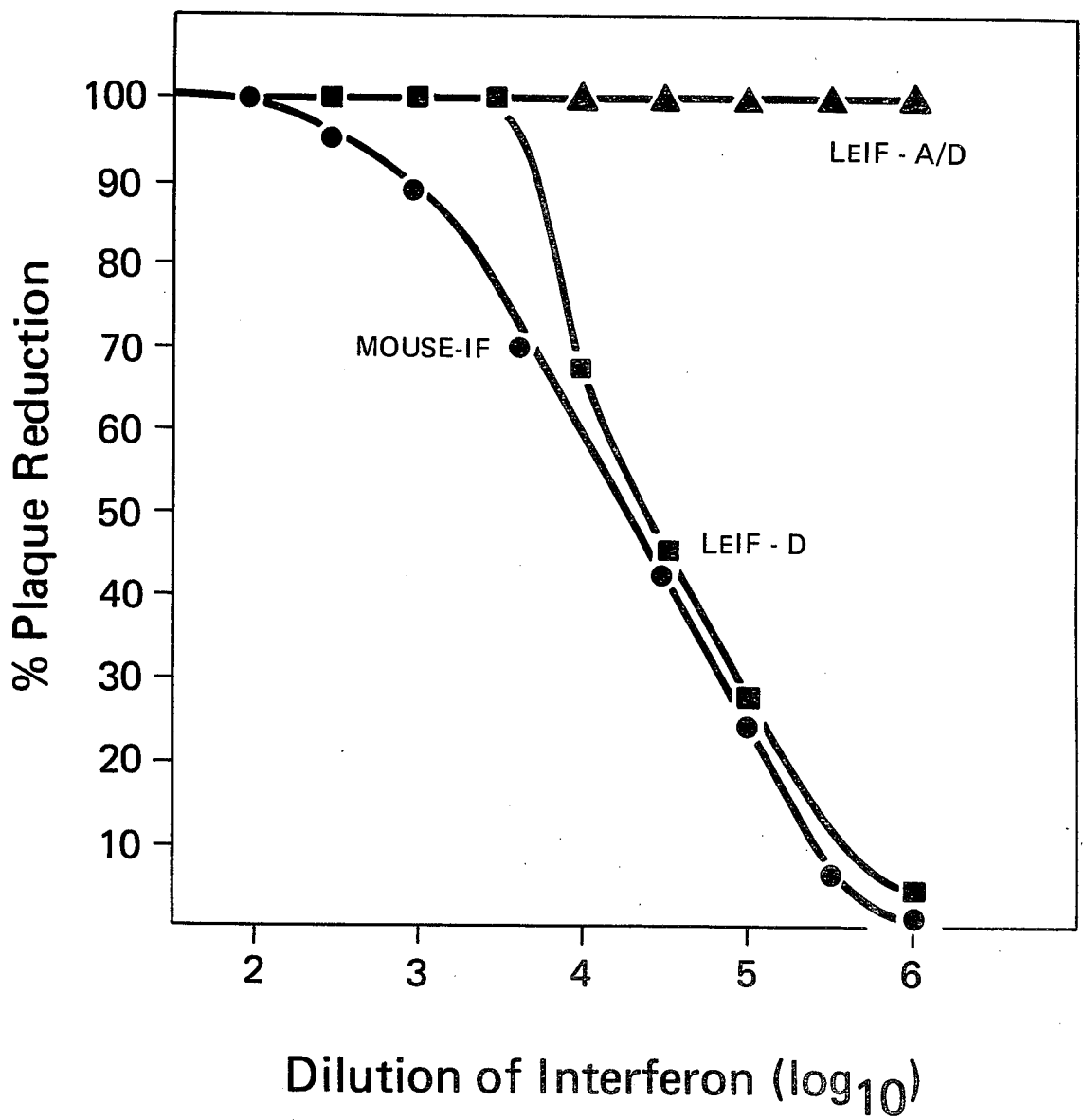
FIGS. 5 and 6 illustrate the results of comparative testing of a preferred hybrid leukocyte interferon of the invention ("LeIF-A/D") for activity against encephalomyocarditis virus ("EMC") and vesicular stomatitis virus ("VSV"), respectively in mouse cells.
Figure 6:
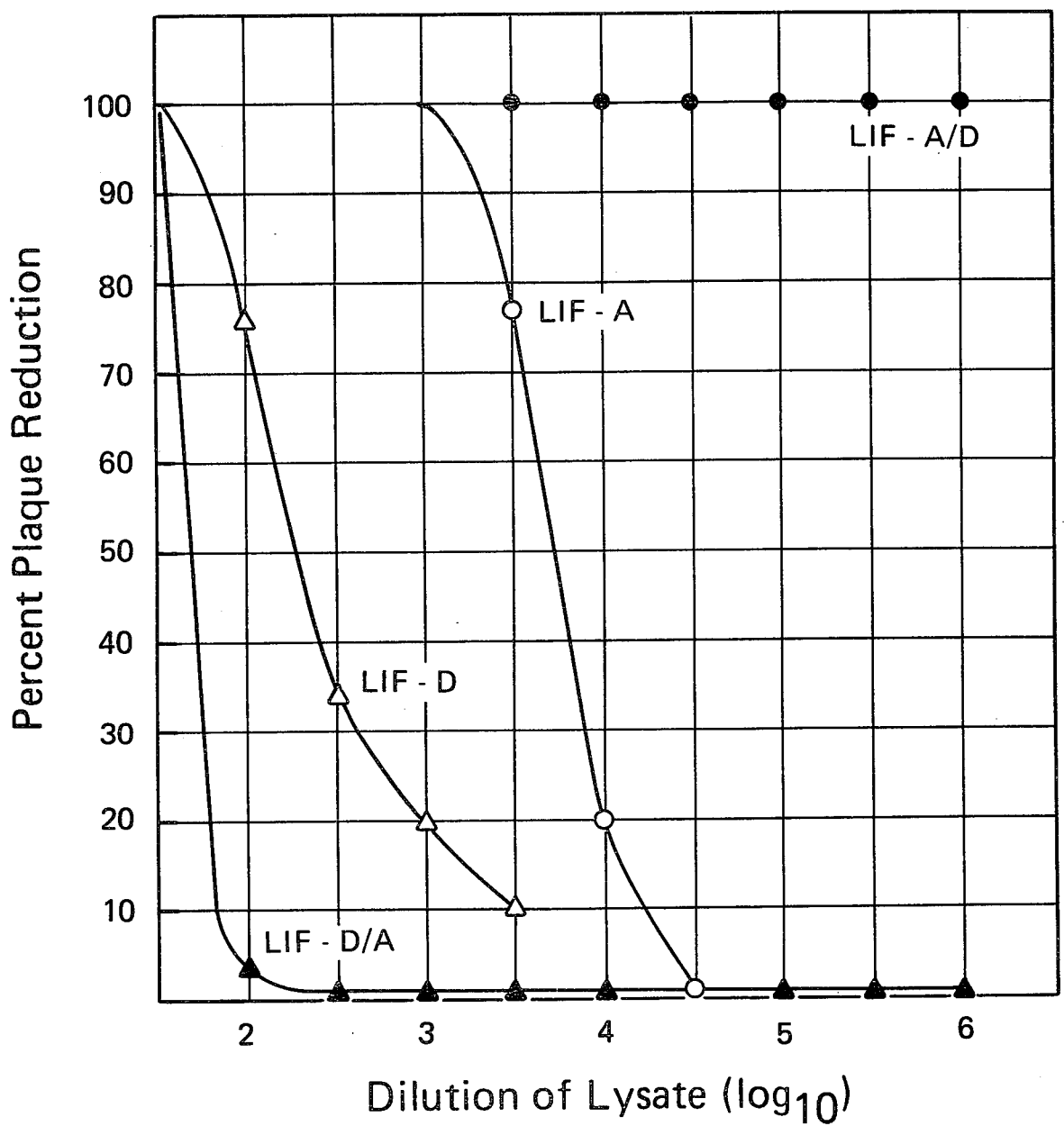
Figure 7:
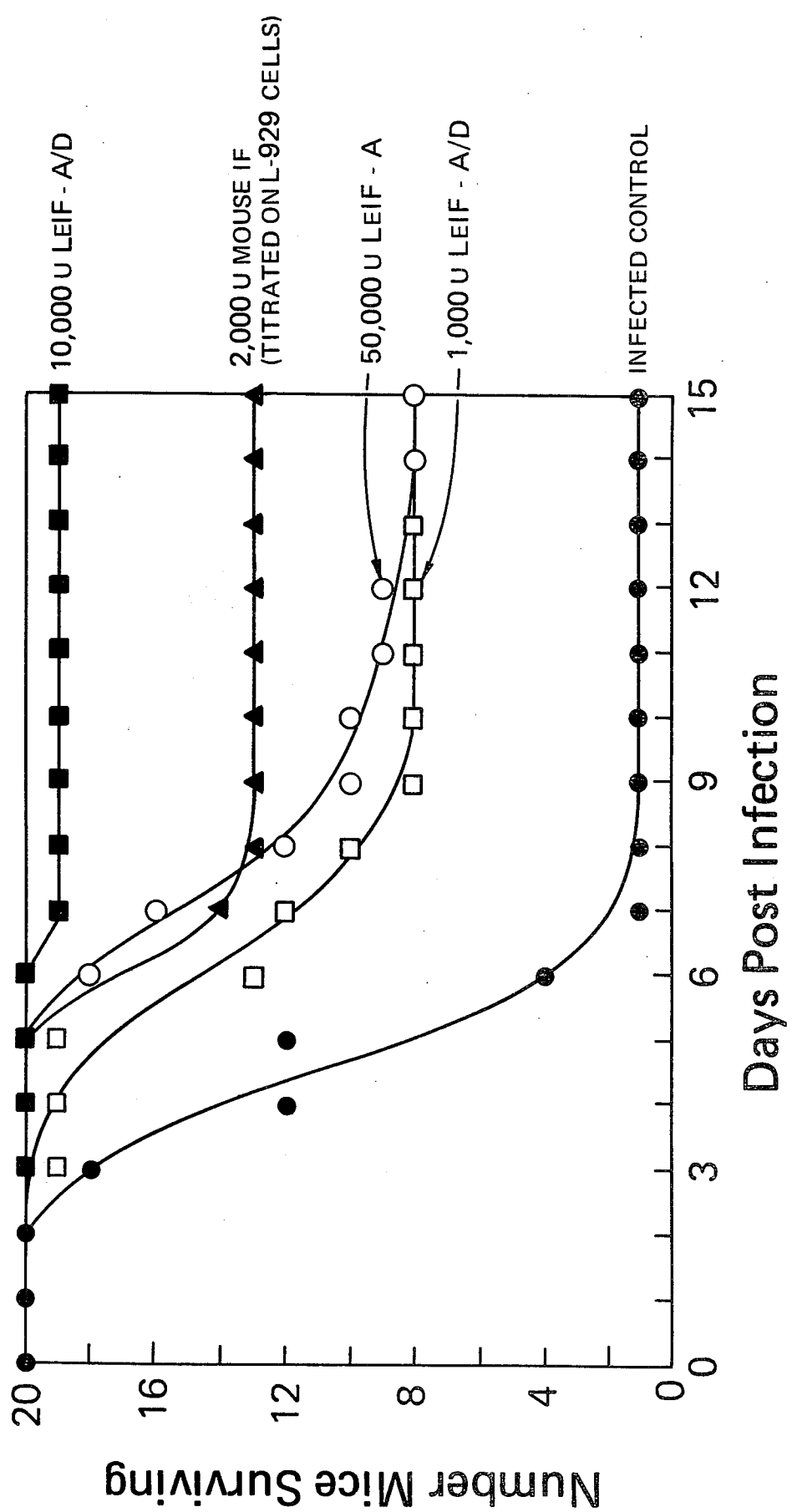
FIGS. 7 and 8 depict the results of comparative testing involving LeIF-A/D and other interferons against EMC virus infections in, respectively, mice and hamsters. The data in FIG. 7 result from treatments i.p. 3 hrs. before infection. Dosages of LeIF-A/D and LeIF-A are as titrated on WISH cells.

The activity of LeIF-A/D against other viruses was also examined. The data in FIG. 5 show antiviral effects against EMC virus infection of L-cells and the data in FIG. 6 shows effects against VSV infection of L-cells. It is clear from these data that the greater activity of LeIF-A/D is not confined to one virus (VSV) and its greater activity is likely to be a general property against many viruses. Natural human buffy-coat interferon preparations have no effect against mouse cells (see Table 2). The activity of LeIF-A/D against EMC virus infection of CD-1 mice was therefore examined. The results in FIG. 7 show that LeIF-A/D is extremely potent against lethal EMC virus infection and LeIF-A also has antiviral activity, as is to be expected from the activity in cell lines (Table 2). The data in FIG. 7 result from treatments i.p. 3 hrs. before infection. Dosages of LeIF-A/D and LeIF-A are as titrated on WISH.

Figure 8:
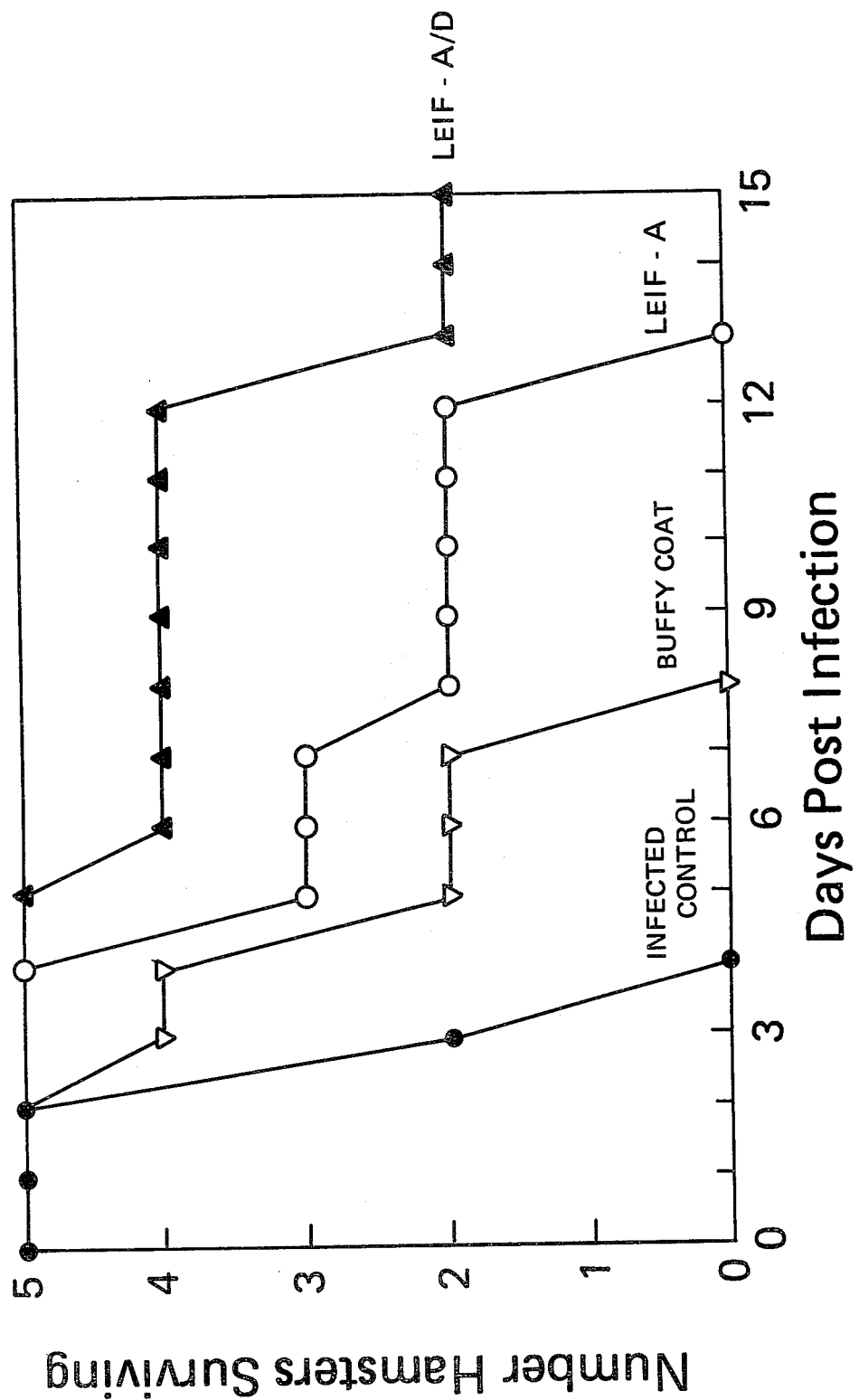

Lethal EMC virus infection of hamsters is also affected by LeIF-A/D and LeIF-A (FIG. 8), the former being the most effective, and buffy coat interferon shows only a small and statistically insignificant effect. In the case of FIG. 8, all interferons were given i.p. 3 hrs. before infection at a dose of $5 \times 10^5$ μ/kg, titrated on WISH cells.

These results indicate that the pronounced antiviral effects of LeIF-A/D in a range of mammalian species is not confined to cell cultures but is also observed in lethal virus infections.

EMC virus can be considered a model system, a demonstration of antiviral effect against which may be predictive of antiviral effect against the represented family of viruses, e.g., the picornavirus family of which foot and mouth disease and polio are members. VSV virus can be considered a model system, a demonstration of antiviral effect against which may be predictive of antiviral effect against the represented family of viruses, e.g., the rhabdovirus family of which rabies is an important member.

Table 4 tabulates the activities of various of the LeIF hybrids hereof on WISH and MDBK cells and the activity ratios thereof:

TABLE 4

| LeIF Hybrid (PvuII) | Units/liter culture WISH Cells | Units/liter culture MDBK Cells | Ratio Activities WISH/MDB |
|---|---|---|---|
| AB | $2.4 \times 10^8$ | $4 \times 10^7$ | 6 |
| AD | $1.2 \times 10^8$ | $2 \times 10^7$ | 6 |
| AF | $6 \times 10^7$ | $1 \times 10^7$ | 6 |
| AG | $4 \times 10^7$ | $1.5 \times 10^7$ | 2.7 |
| AI | $3.2 \times 10^7$ | $1.2 \times 10^7$ | 2.7 |
| BA | $1.5 \times 10^7$ | $1 \times 10^7$ | 1.5 |
| BD | $6 \times 10^7$ | $1.5 \times 10^7$ | 4 |
| BF | $1 \times 10^6$ | $3.5 \times 10^5$ | 0.3 |
| BG | $2 \times 10^7$ | $6 \times 10^7$ | 0.3 |
| DA | $3 \times 10^6$ | $1.2 \times 10^8$ | 0.025 |
| DB | $2 \times 10^6$ | $5 \times 10^7$ | 0.04 |
| DF | $2 \times 10^5$ | $4 \times 10^6$ | 0.05 |
| DG | $2 \times 10^5$ | $1.5 \times 10^7$ | 0.014 |
| FA | $2 \times 10^5$ | $6 \times 10^7$ | 0.003 |
| FB | $2 \times 10^6$ | $8 \times 10^7$ | 0.025 |
| FD | $1 \times 10^7$ | $2 \times 10^7$ | 0.5 |
| FG | $1 \times 10^6$ | $4 \times 10^7$ | 0.025 |
| IA | $2.4 \times 10^6$ | $6 \times 10^7$ | 0.04 |
| A* | $8 \times 10^7$ | $1.2 \times 10^8$ | 0.7 |
| B* | $8 \times 10^7$ | $4 \times 10^8$ | 0.2 |
| C* | $2 \times 10^7$ | $1.5 \times 10^7$ | 1.3 |
| D* | $5 \times 10^6$ | $2.5 \times 10^7$ | 0.2 |
| F* | $2 \times 10^7$ | $2 \times 10^8$ | 0.1 |
| I* | $1.6 \times 10^7$ | $1.2 \times 10^7$ | 1.3 |

*For comparison purposes

PARENTERAL ADMINISTRATION

The hybrid leukocyte interferons hereof may be parenterally administered to subjects requiring antitumor, or antiviral treatment, and to those exhibiting immunosuppressive conditions. Dosage and dose rate may parallel that currently in use in clinical investigations of human derived materials, e.g., about $(1-10) \times 10^6$ units daily, and in the case of materials of purity greater than 1 percent, likely up to, e.g., $50 \times 10^6$ units daily. Preliminary indications in the monkey study described above suggest that dosages of bacterially obtained Le-IF could be significantly elevated for greater effect owing to the essential absence of human proteins other than Le-IF, which proteins in leukocyte-derived materials may act as pyrogens, exhibiting adverse effects, e.g., malaise, temperature elevation, etc.

As one example of an appropriate dosage form for essentially homogeneous bacterial Le-IF in parenteral form applicable herein mutatis mutandis, 3 mg. Le-IF of specific activity of, say, $2 \times 10^8$ U/mg may be dissolved in 25 ml. 5N serum albumin (human)-USP, the solution passed through a bacteriological filter and the filtered solution aseptically subdivided into 100 vials, each containing $6 \times 10^6$ units pure interferon suitable for parenteral administration. The vials are preferably stored in the cold ($-20°$ C.) prior to use.

The compounds of the present invention can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host.

I claim:

1. Double stranded DNA comprising a strand encoding a polypeptide of approximately 165–166 amino acids, the amino acid sequence of said polypeptide comprising, in sequence, discrete sub-sequences corresponding in amino acid identity and number to sub-sequences of different, naturally, occurring leukocyte interferons, the amino acid sequence of said polypeptide differing in overall sequence from the amino acid sequence of naturally occurring leukocyte interferons.

2. The double stranded DNA of claim 1 wherein the encoded polypeptide constitutes a conjugate of substantial amino acid sequences drawn from two or more different leukocyte interferons selected from the group consisting of LeIF A, LeIF B, LeIF C, LeIF D, LeIF E, LeIF F, LeIF G, and LeIF H.

3. The double stranded DNA of claim 2 wherein said encoded polypeptide is selected from the group consisting of LEIF-A/D, LEIF-D/A, LEIF-A/B, LEIF-A/F, LEIF-A/G, LEIF-A/I, LEIF-B/A, LEIF-B/D, LEIF-B/F, LEIF-B/G, LEIF-D/B, LEIF-D/F, LEIF-D/G, LEIF-F/A, LEIF-F/B, LEIF-F/D, LEIF-F/G, and LEIF-I/A.

4. The double stranded DNA of claim 3 which encodes a polypeptide of the sequence LeIF AD (Pvu II).

5. The double stranded DNA of claim 3 wherein said encoded polypeptide is of the sequence LeIF AD (Bgl II).

* * * * *